(12) United States Patent
Troppmann et al.

(10) Patent No.: US 8,741,809 B2
(45) Date of Patent: *Jun. 3, 2014

(54) LIQUID PYRACLOSTROBIN-CONTAINING CROP PROTECTION FORMULATIONS

(75) Inventors: Ulrike Troppmann, Schifferstadt (DE); Wolfgang Meier, Limburgerhof (DE); Guenter Oetter, Frankenthal (DE); Ulrich Steinbrenner, Neustadt (DE); Tatjana Levy, Mannheim (DE); Jurith Montag, Limburgerhof (DE); Tanja Brunner, Obrigheim (DE); Reiner Weiler, Freisbach (DE)

(73) Assignee: BASF SE, Ludwigshafen (DE)

( * ) Notice: Subject to any disclaimer, the term of this patent is extended or adjusted under 35 U.S.C. 154(b) by 274 days.

This patent is subject to a terminal disclaimer.

(21) Appl. No.: 13/123,142

(22) PCT Filed: Oct. 9, 2009

(86) PCT No.: PCT/EP2009/063197
§ 371 (c)(1),
(2), (4) Date: Apr. 7, 2011

(87) PCT Pub. No.: WO2010/040835
PCT Pub. Date: Apr. 15, 2010

(65) Prior Publication Data
US 2011/0195846 A1    Aug. 11, 2011

(30) Foreign Application Priority Data
Oct. 10, 2008 (EP) .................... 08166375

(51) Int. Cl.
*A01N 43/56* (2006.01)
*A01N 25/02* (2006.01)
*A01N 47/02* (2006.01)

(52) U.S. Cl.
USPC ........... 504/280; 504/100; 504/282; 504/302; 504/304; 504/322; 514/406; 514/407; 548/366.1; 548/371.1; 562/8; 562/19; 562/21; 562/23; 564/305

(58) Field of Classification Search
USPC .......... 504/280, 282, 302, 304, 322; 514/406, 514/407; 548/366.1, 371.1; 562/8, 19, 21, 562/23; 564/305
See application file for complete search history.

(56) References Cited

U.S. PATENT DOCUMENTS

| | | |
|---|---|---|
| 3,666,785 A | 5/1972 | Sakai et al. |
| 4,272,920 A | 6/1981 | Dawson |
| 4,283,222 A | 8/1981 | Horide et al. |
| 4,541,860 A | 9/1985 | Civilla et al. |
| 4,945,100 A | 7/1990 | Nyfeler et al. |
| 4,973,352 A | 11/1990 | Heinrich et al. |
| 5,045,311 A | 9/1991 | Pinter et al. |
| 5,192,793 A | 3/1993 | Szekely et al. |
| 5,334,585 A | 8/1994 | Derian et al. |
| 5,459,122 A | 10/1995 | Ford et al. |
| 5,869,517 A | 2/1999 | Muller et al. |
| 5,911,915 A | 6/1999 | Fonsny et al. |
| 6,383,984 B1 | 5/2002 | Aven |
| 6,455,471 B1 | 9/2002 | Gubelmann/Bonneau et al. |
| 6,494,082 B1 | 12/2002 | Mizobe |
| 6,602,823 B1 | 8/2003 | Röchling et al. |
| 6,664,213 B1 | 12/2003 | Furusawa et al. |
| 6,737,553 B1 | 5/2004 | Maas et al. |
| 6,838,473 B2 | 1/2005 | Asrar et al. |
| 7,256,317 B2 | 8/2007 | Maas et al. |
| 2002/0098221 A1* | 7/2002 | Taranta et al. ................ 424/405 |
| 2004/0157745 A1 | 8/2004 | Vermeer et al. |
| 2005/0215433 A1 | 9/2005 | Benitez et al. |
| 2007/0066489 A1 | 3/2007 | Vermeer et al. |
| 2008/0153706 A1 | 6/2008 | Frisch et al. |
| 2008/0214683 A1 | 9/2008 | Steinbrenner et al. |
| 2008/0234350 A1 | 9/2008 | Ziegler et al. |
| 2010/0137375 A1 | 6/2010 | Finch |
| 2010/0210461 A1 | 8/2010 | Stoesser et al. |
| 2010/0227763 A1 | 9/2010 | Krapp et al. |
| 2010/0234227 A1* | 9/2010 | Maier et al. ................... 504/138 |

(Continued)

FOREIGN PATENT DOCUMENTS

| | | |
|---|---|---|
| AU | 610388 | 11/1989 |
| CA | 2 068 826 | 11/1992 |

(Continued)

OTHER PUBLICATIONS

Office Action dated Aug. 12, 2013, from in co-pending U.S. Appl. No. 13/122,790.
Karakotov et al., "Tebuconazole/Based Fungicidal Composition," Shchelkovo Agrokhim Stock Chem., Jun. 19, 2003, XP002498611.
Mulqueen, Patrick, J., et al., "Recent Developments in Suspoemulsions", Pestic. Sci., 1990, p. 451/465, vol. 29.
Rhee et al., "Formulation of Parenteral Microemulsion Containing Itraconazole," Arch. Pharm. Res., vol. 30, No. 1, 2007, pp. 114/123.
Shell Chemicals, "Methyl Proxitol Acetate," Mar. 16, 2007, XP007914204.
Skelton et al., "Formulation of Pesticide Microemulsions," Pesticide Formulations and Application Systems, vol. 8, 1988, pp. 36/45, XP002053622.

(Continued)

*Primary Examiner* — Jane C Oswecki
(74) *Attorney, Agent, or Firm* — Brinks Gilson & Lione

(57) ABSTRACT

The present invention relates to a novel liquid formulation for crop protection which comprises a) pyraclostrobin; b) at least one organic solvent S1 with a water solubility of less than 2 g/l at 20° C.; c) at least one organic solvent S2 with a water solubility of at least 2 g/l at 20° C., where S2 comprises at least one solvent S2.1 with a water solubility of more than 200 g/l at 20° C. and optionally at least one solvent S2.2 with a water solubility of 2 to 200 g/l at 20° C.; d) at least one anionic surface-active substance SA1; e) at least one nonionic surface-active substance SA2; and f) water. The invention also relates to the use of the crop protection formulation for treatment of plants and seed, and to corresponding methods.

23 Claims, No Drawings

(56) References Cited

U.S. PATENT DOCUMENTS

| | | | | |
|---|---|---|---|---|
| 2010/0234457 | A1* | 9/2010 | Taranta et al. | 514/520 |
| 2011/0039698 | A1 | 2/2011 | Taranta et al. | |
| 2011/0105333 | A1 | 5/2011 | Israels et al. | |
| 2011/0124590 | A1 | 5/2011 | Sowa et al. | |
| 2011/0195839 | A1* | 8/2011 | Schlotterbeck et al. | 504/100 |
| 2011/0224076 | A1 | 9/2011 | Sowa et al. | |

FOREIGN PATENT DOCUMENTS

| | | | |
|---|---|---|---|
| CA | 1 334 274 | 2/1995 | |
| CA | 2 570 358 | 1/2006 | |
| DE | 69012487 | 2/1995 | |
| DE | 198 57 963 | 6/2000 | |
| EP | 0126430 | 11/1984 | |
| EP | 0160182 | 11/1985 | |
| EP | 0330904 | 9/1989 | |
| EP | 0 341 126 | 11/1989 | |
| EP | 0432062 | 6/1991 | |
| EP | 0505053 | 9/1992 | |
| EP | 0 514 769 | 11/1992 | |
| EP | 0728414 | 8/1996 | |
| EP | 1 140 741 | 10/2001 | |
| EP | 1339281 | 6/2002 | |
| EP | 1347681 | 6/2002 | |
| EP | 1702607 | 9/2006 | |
| EP | 1886560 | 2/2008 | |
| FR | 2609631 | 7/1988 | |
| RU | 20030118054 | * 6/2003 | A01N 25/02 |
| RU | 2238649 | 10/2004 | |
| WO | WO 90/06681 | 6/1990 | |
| WO | WO 90/09103 | 8/1990 | |
| WO | WO 9315605 | 8/1993 | |
| WO | WO 96/01256 | 1/1996 | |
| WO | WO 96/01305 | 1/1996 | |
| WO | WO 99/66300 | 12/1999 | |
| WO | WO 00/35278 | 6/2000 | |
| WO | WO 00/78139 | 12/2000 | |
| WO | WO 02/42488 | 5/2002 | |
| WO | WO 02/43488 | 6/2002 | |
| WO | WO 02/45507 | 6/2002 | |
| WO | WO 03/000053 | 1/2003 | |
| WO | WO 03/022049 | 3/2003 | |
| WO | WO 2005/105285 | 11/2005 | |
| WO | WO 2006/002984 | 1/2006 | |
| WO | WO 2006030006 | 3/2006 | |
| WO | WO 2006/114186 | 11/2006 | |
| WO | WO 2006/136357 | 12/2006 | |
| WO | WO 2007/017501 | 2/2007 | |
| WO | WO 2007028382 | 3/2007 | |
| WO | WO 2007028387 | 3/2007 | |
| WO | WO 2007028388 | 3/2007 | |
| WO | WO 2007/057028 | 5/2007 | |
| WO | WO 2007/110355 | 10/2007 | |
| WO | WO 2008/017378 | 2/2008 | |
| WO | WO 2008/043807 | 4/2008 | |
| WO | WO 2008/061899 | 5/2008 | |
| WO | WO 2009/019299 | 2/2009 | |
| WO | WO 2009/133166 | 11/2009 | |
| WO | WO 2010/010005 | 1/2010 | |
| WO | WO 2010/040834 | 4/2010 | |
| WO | WO 2010/052178 | 5/2010 | |

OTHER PUBLICATIONS

Tomšič et al., "Ternary Systems of Nonionic Surfactant Brij 35, Water and Various Simple Alcohols: Structural Invesitgations by Small/Angle X/ray Scattering and Dynamic Light Scattering," Journal of Colloid and Interface Science, vol. 294, 2006, pp. 194/211.

Office Action dated May 30, 2012, in co-pending U.S. Appl.NO. 13/122,790.

Herms et al., "Pyraclostrobin—more than just a fungicide", Phytomedizin, (2002), p. 18-19, vol. 32.

International Search Report prepared in International Application No. PCT/EP2009/063197, filed Oct. 9, 2009.

International Preliminary Report on Patentability from corresponding International Application No. PCT/EP2009/063197, filed Oct. 9, 2009.

Herms et al., "Pyraclostrobin—more than just a fungicide", Phytomedizin, (2002), p. 18, vol. 32.

* cited by examiner

LIQUID PYRACLOSTROBIN-CONTAINING CROP PROTECTION FORMULATIONS

This application is a National Stage application of International Application No. PCT/EP2009/063197 filed Oct. 9, 2009, the entire contents of which is hereby incorporated herein by reference. This application also claims priority under 35 U.S.C. §119 to European Patent Application No. 08166375.9, filed Oct. 10, 2008, the entire contents of which is hereby incorporated herein by reference.

DESCRIPTION

The present invention relates to liquid crop protection formulations of pyraclostrobin. Moreover, the invention relates to the use of the crop protection formulations for the treatment of plants and seed and to corresponding methods.

Pyraclostrobin (methyl N-[[[1-(4-chlorophenyl)pyrazol-3-yl]oxy]-o-tolyl]-N-methoxy-carbamate) is an active compound for controlling phytopathogenic fungi (see, for example, WO 96/01256 and Herms, S., Seehaus, K., Koehle, H., and Conrath, U. (2002) "Pyraclostrobin—More than just a Fungicide" Phytomedizin 32:17). Pyraclostrobin is an amorphous substance with a low melting point. Owing to this property, it is not suitable for preparing aqueous suspension concentrates in a conventional manner, since the grinding apparatus will get stuck during grinding. For this reason, pyraclostrobin is frequently formulated in the form of emulsifiable concentrates. To date, we also know of crystalline modifications of pyraclostrobin which allow its formulation as suspension concentrate (see WO 06/136357).

However, such formulations of pyraclostrobin come with the general problems associated with emulsifiable concentrates (EC) and suspension concentrates (SC). Thus, aqueous suspension concentrates comprising pyraclostrobin are distinguished by better environmental compatibility and work hygiene compared to corresponding emulsifiable concentrates, but do not have their good application properties. Moreover, the fungicidal activities both of SC and of EC formulations of pyraclostrobin are unsatisfactory and can in each case be raised to a satisfactory level only by adding large amounts of adjuvants.

An alternative to suspension concentrates and emulsifiable concentrates are microemulsions (ME). Microemulsions, in the case of active compound-comprising microemulsions also referred to as ME formulations, are liquid multiphase systems comprising water and at least one organic solvent which is sparingly miscible with water, if at all, and which comprise a disperse phase and a continuous phase, the disperse phase forming droplets or vesicles or else being capable of forming complex structures. Compared to customary emulsions, in microemulsions the mean distance of the phase boundaries, in general the mean particle or droplet size (Z=mean diameter determined by light scattering) of the disperse phase, is smaller by a factor of at least 5 and is generally not above 500 nm, in particular not above 300 nm or even 200 nm, whereas the droplets in emulsions have a mean diameter in the pm range. As a further distinguishing feature, microemulsions are thermodynamically stable and form without the high input of energy required for emulsions. Owing to the small particle size (droplet size) of the disperse phase or the complex channels, microemulsions are optically transparent.

Formulations of organic pesticides in the form of microemulsions usually comprise, in addition to the active compounds to be formulated, water, at least one surfactant and at least one cosolvent or cosurfactant which is generally an organic solvent or a polyalkylene ether of low molecular weight. Since ME formulations comprise water, on application, risks like flammability, toxicity, damage to the environment and costs are reduced compared to emulsifiable concentrates. However, it is difficult to formulate microemulsions of poorly water-soluble active compounds in a way that they are permanently stable with respect to droplet size, uniformity and crystallization tendency of the active compound. In addition, the emulsions or microemulsions obtained on dilution with water should remain stable and have a droplet size which is as small as possible.

WO 02/45507 discloses microemulsion concentrates comprising a hydrophobic agrochemical, an alkyl alkanoate as first solvent, a polyhydric alcohol or a condensate of polyhydric alcohols as second solvent and a surfactant.

WO 08/017378 describes microemulsion concentrates comprising an agrochemically active compound (which is generally a herbicide), an alcoholic solvent having at least 5 carbon atoms, a non-alcoholic solvent and an anionic and a nonionic surfactant.

Accordingly, it is the object of the present invention to provide crop protection formulations which comprise pyraclostrobin and which have advantageous properties, for the treatment of crops and seed. In particular, they should be distinguished by good application properties, good dilutability with water, in particular hard water, high stability, homogeneous active compound distribution and high fungicidal activity.

Surprisingly, these and other objects are achieved by the liquid formulations described below.

Accordingly, the present invention provides a liquid formulation comprising
a) pyraclostrobin;
b) at least one organic solvent LM1 having a solubility in water of less than 2 g/l, in particular less than 1 g/l or at most 0.5 g/l, at 20° C.;
c) at least one organic solvent LM2 having a solubility in water of at least 2 g/l, in particular at least 4 g/l or at least 0.5 g/l, at 20° C., where LM2 comprises at least one solvent LM2.1 having a solubility in water of more than 200 g/l, in particular of at least 300 g/l or at least 400 g/l, at 20° C. and optionally at least one solvent LM2.2 having a solubility in water from 2 to 200 g/l, in particular from 4 to 150 g/l or from 5 to 100 g/l, at 20° C.;
d) at least one anionic surfactant OS1;
e) at least one nonionic surfactant OS2; and
f) water.

Accordingly, further subject matter of the present invention relates to the use of the formulations according to the invention for the treatment of plants or seed, and to corresponding methods.

The formulations according to the invention provide in particular stable aqueous formulations of pyraclostrobin, optionally in combination with other organic water-insoluble active compounds for crop protection, preferably selected from the group consisting of fungicides and insecticides, for the treatment of plants and seed.

Typically, the formulations according to the invention are microemulsions, i.e. the components form a multi-phase system comprising at least one organic phase and one aqueous phase, the mean distances of the phase boundaries, as a rule the mean particle diameter or droplet size (Z=mean diameter determined by light scattering) of the disperse phase, being in general not more than 500 nm, in particular not more than 300 nm or even 200 nm. In contrast to suspension concentrates, the active compound (pyraclostrobin) in the formulations according to the invention is not in solid, but in dissolved form. Therefore, the formulations according to the invention can also be referred to as ME formulations.

The invention has a number of advantages. Thus, the formulations according to the invention are optically transparent homogeneous formulations which are stable even on prolonged storage and do not tend to form solids. In general, they remain liquid at temperatures down to −10° C., without losing their advantageous properties.

The dynamic viscosity of the formulations according to the invention will generally not exceed a value of 0.5 Pa·s (at 20° C.) and at 20° C. is frequently in the range from 1 to 500 mPa·s and in particular in the range from 2 to 200 mPa·s.

Moreover, the formulations according to the invention can be diluted with water without the particle size increasing to above 500 nm. Finally, they are distinguished by high fungicidal activity. Prior to application, for example, the formulations according to the invention may also simply be diluted with large amounts of water, for example with from 5 to 1000 parts of water per part of the formulation, in particular from 10 to 500 parts of water per part of the formulation. The dilutions usually have high physical stability, i.e. creaming or the formation of sediment is not observed even on prolonged storage, for example for 24 h at room temperature. In this context, the quality of the water used for dilution is of minor importance, which means that for example tap water or spring water can be employed. On dilution with water, the formulations according to the invention generally form turbid or even clear liquids, which shows that the droplets/particles dispersed therein are very small. The mean diameter of the droplets/particles is usually not more than 500 nm, frequently not more than 200 nm, in particular not more than 100 nm and specifically not more than 50 nm; it may be 10 nm or even less. The small particle size remains even after prolonged storage, for example, the particle size after 24 h at room temperature is generally still less than 500 nm.

The average particle diameters mentioned herein represent Z averages of the particle diameters which can be determined by light scattering. Relevant methods with which the skilled person is familiar are described for example in H. Wiese (D. Distler, author), Wässrige Polymerdispersionen [Aqueous polymer dispersions], Wiley-VCH 1999, Chapter 4.2.1, p. 40ff, and in the literature cited therein; H. Auweter, D. Horn, J. Colloid Interf. Sci. 105 (1985), p. 399; D. Lilge, D. Horn, Colloid Polym. Sci. 269 (1991), p. 704 and H. Wiese, D. Horn, J. Chem. Phys. 94 (1991), p. 6429. As a result of the small particle size after dilution with water, the bioavailability, and thus the biological activity, is frequently increased in comparison with traditional formulations.

The terms "alkyl", "alkenyl", "alkylene", "aryl" used below are in each case collective terms for certain organic radicals. In this context, the prefix $C_n$-$C_m$ indicates in each case the total number of carbon atoms of the respective organic radical. In regard of solvents, the prefix $C_n$-$C_m$ indicates in each case the total number of the carbon atoms of the respective organic solvent, with the exception of the N-methyl-substituted heterocyclic solvents such as N-methyllactams and N-methyl- or N,N-dimethylureas, where the prefix $C_n$-$C_m$ indicates in each case the total number of the carbon atoms of the heterocycle; also excepted are the trialkyl phosphates and the mono, di- and trialkyloxy alkanols, where the prefix $C_n$-$C_m$ indicates in each case the number of carbon atoms of the individual alkyl or alkanediyl radicals.

The term "alkyl" refers to saturated straight-chain, branched or cyclic hydrocarbon radicals having the number of carbon atoms stated in the prefix. Accordingly, $C_1$-$C_7$-alkyl refers to saturated straight-chain, branched or cyclic hydrocarbon radicals having 1 to 7 carbon atoms, such as, for example, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, cyclopentyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclohexyl, methylcyclopentyl, heptyl, 1-methylhexyl, 2-methylhexyl, 3-methylhexyl, 4-methylhexyl, 1,1,3-trimethylbutyl, 1,2-dimethylpentyl, 1,3-dimethylpentyl, 2,2-dimethylpentyl, 2,3-dimethylpentyl, 3,3-dimethylpentyl, 3,4-dimethylpentyl, 1-ethylpentyl, 2-ethylpentyl, 1,1,2-trimethylbutyl, 1,2,2-trimethylbutyl, 1-ethyl-1-methylbutyl, 1-ethyl-2-methylbutyl, methylcyclohexyl, 1,2-dimethylcyclopentyl, 1,3-dimethylcyclopentyl and ethylcyclopentyl.

The term "$C_2$-$C_4$-alkylene" refers to saturated, divalent straight-chain or branched hydrocarbon radicals having 2, 3, or 4 carbon atoms, such as, for example, ethane-1,2-diyl, propane-1,3-diyl, propane-1,2-diyl, 2-methylpropane-1,2-diyl, butane-1,4-diyl, butane-1,3-diyl (=1-methylpropane-1,3-diyl), butane-1,2-diyl and butane-2,3-diyl.

The term "aryl" refers to aromatic radicals including heteroaromatic radicals having 1 or 2 heteroatoms selected from the group consisting of O and N, such as, for example, phenyl, naphthyl, anthracenyl, pyridyl, pyrryl, pyrazinyl, pyrimidinyl, purinyl, indolyl, quinolyl, isoquinolyl, imidazolyl, pyrazolyl, indazolyl, furyl, benzofuryl, isobenzofuryl, morpholinyl, oxazolyl, benzoxazolyl, isoxazolyl and benzisoxazolyl.

The formulations according to the invention comprise at least one solvent LM1 having a solubility in water of less than 2 g/l, preferably less than 1 g/l and in particular at most 0.5 g/l, at 20° C. Solvent LM1 can be selected from a multiplicity of nonpolar solvents such as, for example, aliphatic or aromatic hydrocarbons, vegetable oils, fatty acids and their derivatives. The solvent LM1 is preferably selected from the group consisting of aliphatic, aromatic and cycloaliphatic hydrocarbons having boiling points of from 100 to 310° C., $C_8$-$C_{20}$-alkylphenols, $C_8$-$C_{20}$-alkanols, alkyl $C_{10}$-$C_{20}$-alkanecarboxylates, alkyl $C_9$-$C_{20}$-hydroxyalkanecarboxylates, alkyl $C_{12}$-$C_{28}$-cycloalkanecarboxylates, dialkyl $C_{12}$-$C_{28}$-cycloalkanedicarboxylates, $C_{10}$-$C_{15}$-dialkyl dicarboxylates, C25-$C_{35}$-alkanetriol alka-noates, N-octylpyrrolidone, $C_8$-$C_{26}$-fatty acids, in particular $C_{12}$-$C_{20}$-fatty acids, their dialkyl amides, e.g. their di-$C_1$-$C_4$-alkyl amides such as the dimethyl amides, and their alkyl esters, e.g. their $C_1$-$C_8$-alkyl esters such as the methyl and ethyl esters.

In the present context, aliphatic hydrocarbons having boiling points of from 100 to 310° C., in particular from 120 to 280° C. (at atmospheric pressure), refer in particular to straight-chain and branched alkanes or alkenes which have 7 to approximately 18 carbon atoms and which at atmospheric pressure have a boiling point in the abovementioned range, in particular also mixtures of these aliphatic hydrocarbons. Such mixtures are commercially available for example under the trade name Exxsol, this being products which comprise mainly petroleum whose aromatic constituents have been depleted, such as, for example, Exxsol D30, Exxsol D40, Exxsol D80, Exxsol D100, Exxsol D120 and Exxsol D220/230.

In the context of the present invention, aromatic hydrocarbons having boiling points of from 100 to 310° C., in particular from 120 to 280° C. (at atmospheric pressure), are understood as meaning mono- and polycyclic aromatics which optionally have attached to them one or more aliphatic or araliphatic substituents, in particular alkyl or arylalkyl radicals, and which at atmospheric pressure have a boiling point in the abovementioned region. This is preferably understood as meaning mixtures of those aromatic hydrocarbons which are obtained as fractions in the distillation of, in particular, mineral oil products in the abovementioned boiling point range, such as the commercially available products which are known by the trade names Solvesso®, in particular Solvesso® 100, Solvesso® 150, Solvesso® 200, Solvesso® 150 ND, Solvesso® 200 ND, Aromatic®, in particular Aromatic® 150 and Aromatic® 200, Hydrosol®, in particular Hydrosol® A 200 and Hydrosol® A 230/270, Caromax®, in particular Caromax® 20 and Caromax® 28, Aromat K 150, Aromat K 200, Shellsol®, in particular Shellsol® A 100 and Shellsol® A 150, and Fin FAS-TX, in particular Fin FAS-TS 150 and Fin FAS-TX 200. Particular preference is given to the mixtures Solvesso® 150 ND and Solvesso® 200 ND (Exxon-Mobil Chemical), in which the potential carcinogen naphthalene has been depleted. Thus, Solvesso® 150 ND comprises mainly aromatic hydrocarbons having 10 or 11 carbons which boil in the range from 175 to 209° C. and which are in particular alkylbenzenes, whereas Solvesso® 200 ND comprises mainly aromatic hydrocarbons having 10 to 14 carbons which boil in the range from 235 to 305° C. and which are in particular alkylnaphthalenes. A further example of the aromatic hydrocarbons mentioned here is a product known under the trade name Hisol SAS-296, which is a mixture of 1-phenyl-1-xylylethane and 1-phenyl-1-ethylphenylethane.

In the context of the present invention, cycloaliphatic hydrocarbons having boiling points of from 100 to 310° C., in particular from 120 to 280° C. (at atmospheric pressure), are understood as meaning saturated and unsaturated hydrocarbons comprising a non-aromatic carbocycle, and also mixtures of such hydrocarbons. An example is limonene.

The term $C_8$-$C_{20}$-alkylphenol refers to a phenol substituted at the ring by at least one alkyl radical, where $C_8$-$C_{20}$-alkylphenol comprises 8 to 20 carbon atoms. Examples are ethylphenol, 2-methyl-4-ethylphenol, diheptylphenol and dodecylphenol.

$C_8$-$C_{20}$-Alkanols are understood here as meaning alkanols having 8 to 20 and in particular 8 to 14 carbon atoms (=$C_8$-$C_{14}$-alkanols). Examples are octanol, decanol, dodecanol, tridecanol, nonanol, isononanol, 2-propylheptanol, isotridecanol and ethylhexanol.

Alkyl $C_{10}$-$C_{20}$-alkanecarboxylates are understood here as meaning in particular $C_1$-$C_9$-alkanecarboxylic acids esterified with alkanols, where the total number of carbon atoms is from 10 to 20. Examples are ethylhexyl acetate, n-nonyl acetate, isobornyl acetate, propylheptyl isopropionate, n-decyl butyrate, tert-butyl hexanoate, n-pentyl-4-ethyl octanoate and ethyl nonanoate.

Alkyl $C_9$-$C_{20}$-hydroxyalkanecarboxylates are understood here as meaning in particular hydroxylated alkanecarboxylic acids esterified with alkanols, in particular esterified lactic acid (lactates), where the total number of carbon atoms is from 9 to 20. The alkyl radical frequently has 3 to 10 carbon atoms. Examples are tert-butyl 3-hydroxydecanoate, n-propyl 4-hydroxyoctanoate, isopropylhexyl 4-hydroxyoctanoate, ethyl 3-propyl-4-hydroxylhexanoate, n-pentyl 4-hydroxybutyrate, ethylhexyl 3-hydroxybutyrate, 2-ethyl-pentyl lactate, decyl lactate, ethylhexyl lactate, n-heptyl hydroxyacetate, cyclohexylethyl hydroxyacetate and 3-isopropylcyclopentyl hydroxyacetate.

Alkyl $C_{12}$-$C_{28}$-cycloalkanecarboxylates and dialkyl $C_{12}$-$C_{28}$-cycloalkanedicarboxylates are understood here as meaning cycloalkanes substituted by one and two carboxyl groups, respectively, which are esterified by one and two alkanols, respectively, where the total number of carbon atoms is from 12 to 28. Examples are hexyl cyclopentanecarboxylate, pentyl cyclohexanecarboxylate, 3-isopropylhexyl cyclohexanecarboxylate, dibutyl 1,2-cyclopentanedicarboxylate, ethyl butyl 1,3-cyclopentanedicarboxylate, didecyl 1,2-cyclohexanedicarboxylate, methyl octyl 1,4-cyclohexanedicarboxylate and diisononyl cyclohexanedicarboxylate.

$C_{10}$-$C_{15}$-Dialkyl dicarboxylate is understood here as meaning a diester of an alkanedicarboxylic acid having two alkanols, where the total number of carbon atoms is from 10 to 15. The alkyl radicals frequently have in each case 2 to 8 carbon atoms. Examples are butyl hexyl oxalate, dipentyl oxalate, diisobutyl malonate, dihexyl malonate, ethyl pentyl malonate, dipropyl succinate, diisopropyl succinate, diisobutyl succinate, dipentyl succinate, diisopropyl glutarate, diisobutyl glutarate, ethyl pentyl glutarate, dicyclopentyl glutarate, diisobutyl adipate, ethyl propyl adipate, diisobutyl pimelate and diethyl pimelate.

$C_{25}$-$C_{35}$-Alkanetriol alkanoate is understood here as meaning an alkanetriol esterified by three alkanoic acids, where the $C_{25}$-$C_{35}$-alkanetriol alkanoate comprises 25 to 35 carbon atoms. An example is Myritol® 312 (Cognis), which is a mixture of triglycerides having $C_8$-$C_{10}$-fatty acid radicals.

In the present context, $C_8$-$C_{26}$-fatty acids are understood as meaning fatty acids with 8 to 26 carbon atoms. Examples are the saturated fatty acids caprylic acid, capric acid, lauric acid, myristic acid, palmitic acid, margaric acid, stearic acid, arachidic acid, behenic acid, lignoceric acid and cerotic acid; and the monounsaturated fatty acids undecylenic acid, palmitoleic acid, oleic acid, elaidic acid, vaccenic acid, icosenoic acid, cetoleic acid, erucic acid and nervonic acid; and the polyunsaturated fatty acids linoleic acid α-linolenic acid, γ-linolenic acid, arachidonic acid, timnodonic acid, clupanodonic acid and cervonic acid. Examples of dialkylamides of the $C_8$-$C_{26}$-fatty acids are their di-$C_1$-$C_4$-alkylamides, e.g. the dimethylamides, diethylamides, dipropylamides, diisopropylamides, dibutylamides, diisobutylamides, methylethylamides, methylpropylamides, methylisobutylamides, methyl-tert-butylamides, ethylpropylamides, ethylisopropylamides, ethylbutylamides, ethylisobutylamides, propylisopropylamides, propylbutylamides and propylisobutylamides of the abovementioned fatty acids, where the dimethylamides are particularly preferred. Examples of alkyl esters of the $C_8$-$C_{26}$-fatty acids are their $C_1$-$C_8$-alkyl esters, e.g. the methyl esters, ethyl esters, propyl esters, isopropyl esters, butyl esters, isobutyl esters, tert-butyl esters, 1-methyl propyl esters, pentyl esters, 1-methyl butyl esters, 2-methyl butyl esters, 3-methyl butyl esters, hexyl esters, 1-methyl pentyl esters, 2-methyl pentyl esters, 1-ethyl butyl esters and 1,2-dimethyl butyl esters, heptyl esters, 1-methyl hexyl esters, 2-methyl hexyl esters, 3-methyl hexyl esters, 4-methyl hexyl esters, 5-methyl hexyl esters, 1-ethyl pentyl esters, 2-ethyl pentyl esters, 3-ethyl pentyl esters, 4-ethyl pentyl esters, 1,2-dimethyl pentyl esters, 1,3-dimethyl pentyl esters, 1,4-dimethyl pentyl esters, 2,3-dimethyl pentyl esters and ethyl 2-methylbutyl esters of the abovementioned fatty acids, where the methyl and ethyl esters are particularly preferred.

According to a preferred embodiment, the formulations according to the invention comprise at least one solvent LM1 which is selected from $C_8$-$C_{26}$-fatty acids, their di-$C_1$-$C_4$-alkyl amides, e.g. the dimethylamides, $C_{10}$-$C_{15}$-dialkyl dicarboxylates, alkyl $C_9$-$C_{20}$-hydroxyalkanecarboxylates, in particular lactates having a total of 9 to 20 carbon atoms and aromatic hydrocarbons having a boiling point at atmospheric pressure in the range from 100 to 310° C. According to a particularly preferred embodiment, the formulations according to the invention comprise at least one solvent LM1 which is selected from a group consisting of $C_{12}$-$C_{20}$-fatty acids, e.g. the commercial product Edenor® TI 05 (Cognis), which is, according to the manufacturer, a fatty acid mixture with a high oleic acid content, dimethylamides of $C_{12}$-$C_{20}$-fatty acids, e.g. the commercial products Agnique® KE 3658, Agnique® KE 3308, Agnique® AMD 10, Agnique® 810 (Cognis), Genagen 4166, Genagen 4296 (Clariant), Hallcomid M-10 and Hallcomid M-8-10 (Stepan), which are fatty acid dimethylamides or mixtures of these, aromatic hydrocarbons having a boiling point at atmospheric pressure in the range from 120 to 280° C., e.g. Solvesso® 150 ND and Solvesso® 200 ND, and comparable products, $C_6$-$C_{10}$-alkyl lactates having a total of 9 to 13 carbon atoms such as 2-ethylhexyl lactate, and diisobutyl dicarboxylates having a total of 10 to 15 carbon atoms, e.g. technical mixtures of diisobutyl esters of succinic acid, glutaric acid and adipic acid.

The total amount of solvent LM1 which is comprised in the formulations of the invention generally depends on the amounts of pyraclostrobin, surfactants OS1 and OS2, solvents LM2 and optional further ingredients, and also their properties. The weight ratio of solvent LM1 to the total amount of pyraclostrobin is usually in the range of from 0.05:1 to 20:1, preferably in the range of from 0.1:1 to 10:1, and in particular in the range of from 0.5:1 to 5:1. Based on the total weight of the undiluted formulations, the proportion of the solvents LM1 is in general from 0.5 to 40% by weight, preferably from 3 to 30% by weight and in particular from 5 to 20% by weight.

The formulations according to the invention furthermore comprise at least one solvent LM2 having a solubility in water of at least 2 g/l, preferably at least 4 g/l and in particular at least 5 g/l at 20° C., where LM2 comprises at least one solvent LM2.1 having a solubility in water of more than 200 g/l, preferably at least 300 g/l and in particular at least 400 g/l at 20° C. and optionally one or more solvents LM2.2 having a solubility in water of from 2 to 200 g/l, preferably from 4 to 150 g/l and in particular 5 to 100 g/l at 20° C.

A solvent LM2 can be selected from among a large number of weakly polar to polar organic solvents. It is preferably selected from the group consisting of alkoxyalkyl $C_5$-$C_{12}$-alkanecarboxylates, dimethyl sulfoxide (DMSO), $C_3$-$C_6$-alkylene carbonates, N,N'-dimethyl-$C_3$-$C_4$-alkyleneureas, $C_3$-$C_5$-lactones, N-methyl-$C_3$-$C_5$-lactams, tri-$C_1$-$C_4$-alkyl phosphates, alkyl $C_5$-$C_9$-alkanecarboxylates, $C_5$-$C_9$-dialkyl dicarboxylates, $C_5$-$C_9$-ketones, $C_5$-$C_9$-alkanediol alkanoates, $C_5$-$C_9$-alkanetriol alkanoates, $C_1$-$C_7$-alkanols, $C_5$-$C_9$-cycloalkylalcohols, mono-, di- and tri-($C_1$-$C_4$-alkyloxy)-$C_1$-$C_4$-alkanols, aliphatic $C_2$-$C_{10}$-diols, aliphatic $C_3$-$C_{15}$-triols, $C_5$-$C_9$-arylalkyl alcohols, $C_5$-$C_9$-aryloxyalkyl alcohols, hydroxylated $C_5$-$C_8$-alkanecarboxylic esters and tetrahydrofurfuryl alcohol.

Accordingly, a solvent LM2.1 is preferably selected from the group consisting of DMSO, $C_3$-$C_5$-alkylene carbonates, N,N'-dimethyl-$C_3$-$C_4$-alkyleneureas, $C_3$-$C_5$-lactones, N-methyl-$C_3$-$C_5$-lactams, tri-$C_1$-$C_4$-alkyl phosphates, $C_1$-$C_3$-alkanols, mono-, di- and tri-($C_1$-$C_4$-alkyloxy)-$C_1$-$C_4$-alkanols, aliphatic $C_2$-$C_8$-diols, aliphatic $C_3$-$C_{12}$-triols, hydroxylated $C_4$-$C_8$-alkanecarboxylic esters and tetrahydrofurfuryl alcohol. Particularly preferably, LM2.1 is selected from the group consisting of $C_3$-$C_5$-lactones, hydroxylated $C_5$-$C_8$-alkanecarboxylic esters, $C_1$-$C_3$-alkanols, aliphatic $C_2$-$C_8$-diols and aliphatic $C_3$-$C_{12}$-triols, in particular from the group consisting of γ-butyrolactone, n-propyl lactate, 2-methyl-2,4-pentanediol (hexylene glycol), tetrahydrofurfuryl alcohol and propylene glycol.

Correspondingly, a solvent LM2.2 is preferably selected from the group consisting of alkoxyalkyl $C_5$-$C_{12}$-alkanecarboxylates, alkyl $C_5$-$C_9$-alkanecarboxylates, $C_5$-$C_9$-dialkyl dicarboxylates, $C_5$-$C_9$-ketones, $C_5$-$C_9$-alkanediol alkanoates, $C_5$-$C_9$-alkanetriol alka-noates, $C_4$-$C_7$-alkanols, aliphatic $C_7$-$C_{10}$-diols, aliphatic $C_{11}$-$C_{15}$-triols, $C_5$-$C_9$-cycloalkyl alcohols, $C_5$-$C_9$-arylalkyl alcohols and $C_5$-$C_9$-aryloxyalkyl alcohols. Particularly preferably, LM2.2 is selected from the group consisting of $C_5$-$C_9$-ketones and $C_5$-$C_9$-arylalkyl alcohols.

An alkoxyalkyl C5-C12-alkanecarboxylate is understood here as an ester of an alkane-carboxylic acid with an alkoxyalkanol where the total number of carbon atoms is from 5 to 12. Examples are isopropoxymethyl formate, ethylene glycol ethyl ether formate, ethylene glycol butyl ether formate, ethylene glycol 2-methylbutyl ether formate, ethylene glycol pentyl ether formate, isopropoxymethyl formate, isopropoxyethyl formate, isopropoxy-tert-butyl formate, ethoxymethyl acetate, isopropoxymethyl acetate, ethylene glycol methyl ether acetate, ethylene glycol ethyl ether acetate, ethylene glycol propyl ether acetate, ethylene glycol butyl ether acetate, ethylene glycol tert-butyl ether acetate, propylene glycol methyl ether acetate, propylene glycol ethyl ether acetate, propylene glycol propyl ether acetate, propylene glycol isopropyl ether acetate, methoxypropyl acetate, ethoxypropyl acetate, propoxypropyl acetate, isopropoxypropyl acetate, ethylene glycol methyl ether butyrate, ethylene glycol ethyl ether butyrate, propylene glycol methyl ether butyrate, propylene glycol methyl ether 2-methylpropylate, isopropoxymethyl butyrate, propoxymethyl tert-butyrate, methoxypropyl butyrate, methoxypropyl 2-methylpropylate, ethylene glycol methyl ether pentanoate, ethylene glycol methyl ether 3-methylbutyrate, propoxypropyl propionate, butoxyethyl butyrate, propylene glycol pentyl ether acetate, propylene glycol butyl ether pentanoate and pentoxypropyl butyrate.

Here, $C_3$-$C_5$-alkylene carbonates refer in particular to cyclic diesters of carbonic acid having a total of 3, 4 or 5 carbon atoms, such as, for example, ethylene carbonate, 1,2-propylene carbonate, 1,3-propylene carbonate, 1,2-, 1,3-, 1,4- and 2,3-butylene carbonate.

In the context of the present invention, the terms "$C_4$-$C_8$-alkanecarboxylic ester which carries at least one hydroxyl group" and "hydroxylated $C_4$-$C_8$-alkanecarboxylic ester" refer to esters of alkanecarboxylic acids which are esterified with alkanols, where either the alkyl radical originating from the acid or the alkyl radical originating from the alcohol is substituted by at least one hydroxyl group and where the total number of carbon atoms is from 4 to 8. The total number of hydroxyl groups is typically 1 or 2, in particular 1. Examples of hydroxylated alkanecarboxylic acids are 5-hydroxyvaleric acid, 4-hydroxyvaleric acid, 2-hydroxyvaleric acid, 4-hydroxybutyric acid, 3-hydroxybutyric acid, 2-hydroxybutyric acid, 3-hydroxypropionic acid, lactic acid and hydroxyacetic acid. Examples of hydroxylated alkanols are pentane-1,5-diol, pentane-1,3-diol, pentane-2,4-diol, cyclopentane-1,2-diol, butane-1,4-diol, butane-2,3-diol, propane-1,2-diol, 2-(hydroxymethyl)butanol, 2-(hydroxyethyl)propanol, 2-(hydroxymethyl)propanol and ethane-1,2-diol. Examples of hydroxylated $C_5$-$C_8$-alkanecarboxylic esters are n-butyl 4-hydroxybutyrate, isobutyl 3-hydroxybutyrate, n-propyl 4-hydroxybutyrate, isopropyl 4-hydroxybutyrate, isopropyl 3-hydroxybutyrate, methyl 4-hydroxybutyrate, ethyl 4-hydroxybutyrate, 2-ethyl propyl lactate, 2-methylpropyl lactate, n-propyl lactate, isopropyl lactate, n-butyl lactate, isobutyl lactate, ethyl lactate, methyl lactate, cyclopentyl lactate, n-hexyl hydroxyacetate, cyclohexyl hydroxyacetate, 3-methylcyclopentyl hydroxyacetate, n-pentyl hydroxyacetate, 2-methylpentyl hydroxyacetate, n-butyl hydroxyacetate, tert-butyl hydroxyacetate, n-propyl hydroxyacetate, isopropyl hydroxyacetate, 5-hydroxypentyl acetate, 3-hydroxycyclopentyl propionate, 3-hydroxybutyl acetate, 3-hydroxypropyl acetate, 3-hydroxypentyl propionate, 3-hydroxycyclopentyl propionate, 2-hydroxymethylbutyl propionate, 3-hydroxypropyl propionate, 2-hydroxyethyl propionate, 2-hydroxymethylpropyl butyrate, 3-hydroxypropyl butyrate, 2-hydroxyethyl butyrate, 3-hydroxypropyl valerate and 2-hydroxyethyl valerate.

In the context of the present invention, an aliphatic $C_2$-$C_{12}$-diol is understood as meaning an aliphatic straight-chain or branched hydrocarbon which carries 2 hydroxyl groups; for example glycol, 1,2-propanediol, 1,2-but-3-enediol, 1,5-pentanediol, 2,4-pentanediol, 2-methyl-2,4-pentanediol (hexylene glycol), 1,6-hexanediol, 2,5-hexanediol, 1,6-hex-3-enediol, 3-methyl-2,4-hexanediol, 1,7-heptanediol, 2,6-heptanediol, 1,8-octanediol, 2,7-octanediol, 1,3-cyclohexanediol, 1,2-cyclohexanediol, 1,2-cyclohex-4-enediol, 1,4-cyclohexanediol, 1,2-cycloheptanediol, 4-propyl-5-ethyl-1,2-cycloheptanediol, 2-methyl-4,6-decanediol and 1,2-dodecanediol.

In the context of the present invention, an aliphatic $C_3$-$C_{18}$-triol is understood as meaning an aliphatic straight-chain or branched hydrocarbon which carries 3 hydroxyl groups; for example glycerol, 1,2,4-butanetriol, 1,2,3-pentanetriol, 2,3,4-pentanetriol, 1,2,3-hexanetriol, 1,2,5-hexanetriol, 1,2,3-heptanetriol, 1,6,7-heptanetriol, 2,3,6-heptanetriol, 1,2,3-octanetriol, 1,2,3-oct-5-enetriol, 2,3,4-octanetriol, 1,2,8-octanetriol, 2,3,7-octanetriol, 1,2,3-cyclohexanetriol, 1,3,5-cyclohexanetriol, 1,2,4-cyclohexanetriol, 1,2,3-cycloheptanetriol, 1,2,6-cycloheptanetriol, 1,2,3-nonanetriol, 2,5,10-dodecanetriol, 2,4,6-trimethyl-1,8,12-dodecanetriol, 8-heptyl-1,2,3-undecanetriol.

A tri-$C_1$-$C_4$-alkyl phosphate is understood as meaning a triester of phosphoric acid having three $C_1$-$C_4$-alkanols selected independently of one another, for example trimethyl phosphate, triethyl phosphate, tri-n-propyl phosphate, triisopropyl phosphate, tri-n-butyl phosphate, triisobutyl phosphate, methyl diethyl phosphate, dimethyl ethyl phosphate, methyl di-n-propyl phosphate, methyl ethyl n-propyl phosphate, ethyl 2-methylpropyl methyl phosphate, diethyl n-propyl phosphate, dimethyl isobutyl phosphate, diethyl n-butyl phosphate, n-propyl isobutyl n-butyl phosphate and dimethyl tert-butyl phosphate.

An alkyl $C_5$-$C_9$-alkanecarboxylate is understood here as meaning in particular an alkanecarboxylic acid esterified with an alkanol, where the total number of carbon atoms is from 5 to 9. Examples are isopropyl acetate, n-propyl acetate, isobutyl acetate, tert-butyl acetate, n-pentyl acetate, cyclopentyl acetate, n-hexyl acetate, 3-methylcyclopentyl acetate, cyclohexyl acetate, n-heptyl acetate, 3-methylcyclohexyl acetate, n-propyl propionate, isopropyl propionate, n-butyl propionate, tert-butyl propionate, n-pentyl propionate, n-propyl isopropionate, cyclopropyl propionate, cyclopropyl isopropionate, isopropyl isopropionate, n-butyl isopropionate, tert-butyl isopropionate, n-pentyl isopropionate, n-hexyl propionate, cyclohexyl propionate, ethyl butyrate, n-propyl butyrate, isopropyl butyrate, n-butyl butyrate, tert-butyl butyrate, ethyl tert-butyrate, n-propyl tert-butyrate, isopropyl tert-butyrate, n-butyl tert-butyrate, tert-butyl tert-butyrate, n-pentyl butyrate, methyl pentanoate, ethyl pentanoate, propyl pentanoate, isopropyl pentanoate, n-butyl pentanoate, methyl hexanoate, ethyl hexanoate, isopropyl hexanoate, methyl heptanoate, ethyl heptanoate and methyl octanoate.

Here, mono-, di- or tri-($C_1$-$C_4$-alkyloxy)-$C_1$-$C_4$-alkanol refers to a $C_1$-$C_4$-alkanediol which is etherified with a $C_1$-$C_4$-alkanol, a $C_1$-$C_4$-alkyloxy-$C_1$-$C_4$-alkanol or a $C_1$-$C_4$-alkyloxy-$C_1$-$C_4$-alkyloxy-$C_1$-$C_4$-alkanol. Examples are ethylene glycol methyl ether, ethylene glycol ethyl ether, propylene glycol ethyl ether, diethylene glycol methyl ether, dipropylene glycol ethyl ether, triethylene glycol methyl ether and tripropylene glycol butyl ether.

A $C_5$-$C_9$-dialkyl dicarboxylate is understood here as meaning a diester of an alkanedi-carboxylic acid having two alkanols selected independently of one another, where the total number of carbon atoms is from 5 to 9 and in particular 5, 6, 7 or 8. Examples are ethyl methyl oxalate, diethyl oxalate, ethyl propyl oxalate, ethyl isopropyl oxalate, dipropyl oxalate, propyl isopropyl oxalate, ethyl butyl oxalate, methyl pentyl oxalate, propyl butyl oxalate, dimethyl malonate, methyl ethyl malonate, diethyl malonate, propyl ethyl malonate, isopropyl ethyl malonate, methyl propyl malonate, methyl isopropyl malonate, dipropyl malonate, dimethyl succinate, ethyl methyl succinate, diethyl succinate, methyl propyl succinate, methyl isopropyl succinate, ethyl propyl succinate, dimethyl glutarate, ethyl methyl glutarate, diethyl glutarate, dimethyl adipate, ethyl methyl adipate and dimethyl pimelate.

In the context of the present invention, the term "$C_5$-$C_9$-ketones" includes optionally alkoxylated aliphatic, cycloaliphatic and araliphatic ketones having 5 to 9 carbon atoms; these include, for example, 2-pentanone, 3-pentanone, 2-hexanone, 3-hexanone, 2-heptanone, 3-heptanone, 4-heptanone, 2-octanone, 3-octanone, 4-octanone, 4-methyl-2-pentanone, 5-methyl-2-hexanone, cyclopentanone, cyclohexanone, cycloheptanone, cyclooctanone, cyclohexylcarboxymethane, acetophenone and methoxyacetophenone.

A $C_5$-$C_9$-arylalkyl alcohol (=$C_5$-$C_9$-arylalkanol) is understood as meaning an alkanol which is substituted by an aryl radical, the $C_5$-$C_9$-arylalkyl alcohol having a total of 5 to 9 carbon atoms. Examples are benzyl alcohol, 2-phenylethanol, 1-phenylethanol, phenylpropanol, pyridin-1-ylmethanol, pyridin-3-ylmethanol, 1-pyridin-3-ylethanol, pyridinylbutanol, pyrimidin-1-ylmethanol, pyrimidin-1-ylethanol, 2-pyrimidin-3-ylpropanol, furan-2-ylmethanol, 2-furan-2-ylethanol, 3-furan-3-ylpropanol and 4-furan-2-ylbutanol.

A $C_5$-$C_9$-aryloxyalkyl alcohol (=$C_5$-$C_9$-aryloxyalkanol) is understood here as meaning an alkanol substituted by an aryloxy radical, the $C_5$-$C_9$-aryloxyalkyl alcohol having a total of 5 to 9 carbon atoms. Examples are phenoxymethanol and phenoxyisopropanol.

Here, $C_5$-$C_9$-cycloalkyl alcohols refer to cyclic alkanols having 5 to 9 carbon atoms, such as, for example, cyclopentanol, cyclohexanol, cycloheptanol and cyclooctanol.

A $C_5$-$C_9$-alkanediol alkanoate is understood here as meaning an alkanediol esterified with two alkanoic acids, the $C_5$-$C_9$-alkanediol alkanoate having a total of 5 to 9 carbon atoms. Examples are diacetin, glycol diacetate, glycol dipropionate, glycerol dipropionate and propylene glycol diacetate.

A $C_5$-$C_9$-alkanetriol alkanoate is understood here as meaning an alkanetriol esterified with three alkanoic acids, the $C_5$-$C_9$-alkanetriol alkanoate having 5 to 9 carbon atoms. An example is triacetin.

An N,N'-dimethyl-$C_3$-$C_4$-alkyleneurea is understood as meaning doubly N-methylated derivatives of cyclic ureas having 3 or 4 carbon atoms in the ring. An example of N,N'-dimethyl-$C_3$-$C_4$-alkyleneureas is N,N'-dimethylethyleneurea (1,3-dimethylimidazolin-2-one).

A $C_3$-$C_5$-lactone is understood as meaning a cyclic ester of a hydroxycarboxylic acid having 3, 4 or 5 carbon atoms in the ring. An example of $C_3$-$C_5$-lactones is γ-butyrolactone.

An N-methyl-$C_3$-$C_5$-lactam is understood as meaning an N-methylated derivative of a lactam having 3, 4 or 5 carbon atoms in the ring. Examples of N-methyl-$C_3$-$C_5$-lactams are N-methylpyrrolidone and N-methylpiperidone.

In a preferred embodiment, the formulations according to the invention comprise at least one solvent LM2.2 having a solubility in water of from 2 to 100 g/l at 20° C., which is selected, for example, from the group consisting of alkoxyalkyl $C_7$-$C_{12}$-alkanecarboxylates, alkyl $C_5$-$C_9$-alkanecarboxylates, $C_5$-$C_9$-dialkyl dicarboxylates, $C_6$-$C_9$-ketones, $C_5$-$C_9$-alkanediol alkanoates, $C_5$-$C_9$-alkanetriol alkanoates, $C_4$-$C_7$-alkanols, aliphatic $C_8$-$C_{10}$-diols, aliphatic $C_{12}$-$C_{15}$-triols, $C_5$-$C_9$-cycloalkyl alcohols, $C_5$-$C_9$-arylalkyl alcohols and $C_5$-$C_9$-aryloxyalkyl alcohols, preferably selected from the group consisting of $C_6$-$C_9$-ketones and $C_5$-$C_9$-arylalkyl alcohols, in particular from the group consisting of acetophenone, cyclohexanone, 2-heptanone and benzyl alcohol.

In a further preferred embodiment, the formulations according to the invention comprise at least two solvents LM2.1 having a solubility in water of more than 200 g/l, preferably at least 300 g/l and in particular at least 400 g/l at 20° C. According to a particularly preferred embodiment, one of these two solvents LM2.1 is completely water-soluble, and according to an especially preferred embodiment, both solvents LM2.1 in question are completely water-soluble. Such completely water-soluble solvents LM2.1 can be selected, for example, from the group consisting of DMSO, $C_2$-$C_4$-alkylene carbonates, $C_3$-$C_5$-lactones, N-methyl-$C_3$-$C_5$-lactams, $C_1$-$C_3$-alkanols, mono-, di- and tri-($C_1$-$C_3$-alkyloxy)-$C_1$-$C_3$-alkanols, aliphatic $C_2$-$C_6$-diols, aliphatic $C_3$-$C_9$-triols, hydroxylated $C_5$-$C_8$-alkanecarboxylic esters and tetrahydrofurfuryl alcohol, in particular from the group consisting of γ-butyrolactone, n-propyl lactate, DMSO, 2-methyl-2,4-pentanediol and propylene glycol. Examples of the two completely water-soluble solvents LM2.1 according to the last-mentioned embodiment are combinations of a protic solvent LM2.1, preferably an aliphatic $C_2$-$C_6$-diol or aliphatic $C_3$-$C_9$-triol, and a nonprotic solvent LM2.1 such as a hydroxylated $C_5$-$C_8$-alkanecarboxylate or a $C_3$-$C_5$-lactone. Among these combinations, those which consist of propylene glycol or hexylene glycol and γ-butyrolactone or n-propyl lactate are preferred.

According to a further preferred embodiment, the formulations according to the invention comprise at least one solvent LM2.1 which may optionally serve as antifreeze for increasing low-temperature stability. Examples of such solvents LM2.1 are aliphatic $C_2$-$C_6$-diols.

The total amount of solvent LM2 which is comprised in the formulations of the invention generally depends on the amounts of pyraclostrobin, surfactants OS1 and OS2, solvents LM1 and optional further ingredients, and also their properties. The weight ratio of solvent LM2 and the total amount of pyraclostrobin is usually in the range of from 0.05:1 to 30:1, preferably in the range of from 0.1:1 to 10:1, and in particular in the range of from 0.15:1 to 5:1. Based on the total weight of the undiluted formulations, the proportion of the solvents LM2 is in general from 1 to 60% by weight, preferably from 5 to 35% by weight and in particular from 10 to 30% by weight.

In a preferred embodiment, the formulations according to the invention comprise at least one solvent LM1 and at least one, for example one or two, solvents LM2.1. According to a further preferred embodiment, they additionally comprise a solvent LM2.2.

The formulations according to the invention comprise at least one nonionic surfactant OS2 and at least one anionic surfactant OS1. The term surfactant refers to surface-active substances, hereinbelow also referred to as emulsifiers or detergents. The purpose of the surfactants is to reduce the surface tension between the continuous and the disperse phase and thereby to stabilize the particles/droplets of the disperse phase. The surfactants also help to solubilize the pyraclostrobin and optional further organic active compounds for crop protection. The skilled worker is familiar with suitable surfactants for formulating microemulsions, for example through McCutcheon, Detergents and Emulsifiers, Int. Ed., Ridgewood, N.Y. The surfactants may be polymeric or nonpolymeric surfactants. Preferably, the predominant portion, in particular at least 90% and specifically all of the surfactants present in the microemulsion, is selected from the group of the nonpolymeric surfactants, which are also referred to as emulsifiers. Usually, nonpolymeric surfactants (emulsifiers) have an average molecular weight (number average) of up to 9000 Daltons, in particular from 150 to 6000 Daltons and preferably from 200 to 3000 Daltons.

The group of the nonionic surfactants includes in particular:

homo- and copolymers of $C_2$-$C_4$-alkylene oxides, in particular homopolymers of ethylene oxide, copolymers of ethylene oxide with $C_3$-$C_4$-alkylene oxides, in particular ethylene oxide/propylene oxide copolymers; in this context the term "homo- and copolymer" also comprises oligomeric substances having in general at least 5 repeat units;

compounds of the formula

in which n denotes the average number of repeat units [OA] in the range of from 2 to 50, each A in each case independently is ethanediyl, propane-1,2-diyl, butane-1,2-diyl or 2-methylpropane-1,2-diyl, R is straight-chain or branched $C_8$-$C_{24}$-alkyl or $C_8$-$C_{24}$-alkenyl, and R' is H, $C_1$-$C_8$-alkyl, CHO or $C_1$-$C_8$-alkylcarbonyl.

Examples of these are oligo-$C_2$-$C_4$-alkylene oxide $C_8$-$C_{22}$-alkyl ethers, in particular ethoxylates and ethoxylate-co-propoxylates of the straight-chain and branched $C_8$-$C_{22}$-alkanols, preferably ethoxylates and ethoxylate-co-propoxylates of the fatty alcohols and ethoxylates of the oxo alcohols, such as, for example, lauryl alcohol ethoxylate, isotridecanol ethoxylate, cetyl alcohol ethoxylate, stearyl alcohol ethoxylate and their esters, such as, for example, the acetates;

oligo-$C_2$-$C_3$-alkylene oxide aryl ethers and oligo-$C_2$-$C_4$-alkylene oxide $C_1$-$C_{22}$-alkylaryl ethers, such as, for example, oligo-$C_2$-$C_3$-alkylene oxide $C_1$-$C_{16}$-alkylbenzene ethers, in particular ethoxylates of the $C_1$-$C_{22}$-alkylphenols such as, for example, the ethoxylate of nonylphenol, decylphenol, isodecylphenol, dodecylphenol or isotridecylphenol;

oligo-$C_2$-$C_3$-alkylene oxide mono-, di- or tristyrylphenyl ethers, in particular ethoxylates of the mono-, di- and tristyrylphenols, and their condensates with formaldehyde and their esters, such as, for example, the acetates;

$C_6$-$C_{22}$-alkylglucosides and $C_6$-$C_{22}$-alkyloligoglucosides; ethoxylates of the $C_6$-$C_{22}$-alkylglucosides and ethoxylates of the $C_6$-$C_{22}$-alkyloligoglucosides;

ethoxylates of the fatty acids and ethoxylates of the hydroxyl fatty acids;

partial esters of polyols with $C_6$-$C_{22}$-alkanoic acids, in particular mono- and diesters of glycerol and mono-, di- and triesters of sorbitan, such as, for example, glycerol monostearate, sorbitan monododecanoate, sorbitan dioleate and sorbitan tristearate;

ethoxylates of the partial esters of polyols with $C_6$-$C_{22}$-alkanoic acids, in particular ethoxylates of the mono- and diesters of glycerol and ethoxylates of the mono-, di- and triesters of sorbitan, such as, for example, ethoxylates of glycerol monostearate, ethoxylates of sorbitan monooleate, ethoxylates of sorbitan monostearate and ethoxylates of sorbitan tristearate;

ethoxylates of vegetable oils or animal fats, such as, for example, corn oil ethoxylate, castor oil ethoxylate, tall oil ethoxylate;

acetylene glycols such as, for example, 2,4,7,9-tetramethyl-4,7-dihydroxy-5-decine;

ethylene oxide/propylene oxide block copolymers; and ethoxylates of fatty amines or of fatty acid diethanolamides.

The term oligo-$C_2$-$C_4$-alkylene oxide ether or oligo-$C_2$-$C_4$-alkylene oxide refers to oligoether radicals which are derived from $C_2$-$C_4$-alkylene oxides such as ethylene oxide, propylene oxide (=1-methyloxirane), 1,2-butylene oxide (=1-ethyloxirane) and 2-methylpropylene oxide (=1,1-dimethyloxirane). Accordingly, the term oligo-$C_2$-$C_3$-alkylene oxide ether refers to oligoether radicals which are derived from $C_2$-$C_3$-alkylene oxides such as ethylene oxide and propylene oxide. The term ethoxylate refers to oligoether radicals which are derived from ethylene oxide. Analogously, the term oligoethylene oxide co-oligopropylene oxide refers to polyether radicals which are derived from mixtures of ethylene oxide and propylene oxide. The number of repeat units in the oligoether radicals is generally between 2 and 120, frequently between 4 and 80, and in particular between 5 and 60.

Among the abovementioned nonionic surfactants, the following are preferred:

homo- or copolymers of the $C_2$-$C_3$-alkylene oxides;

compounds of the formula I:

R—[OA]$_n$-OR'  (I), in which n denotes the average number of repeat units [OA] in the range of from 2 to 50, each A in each case independently is ethanediyl, propane-1,2-diyl, butane-1,2-diyl or 2-methylpropane-1,2-diyl, R is straight-chain or branched $C_8$-$C_{24}$-alkyl or $C_8$-$C_{24}$-alkenyl, and R' is H, $C_1$-$C_8$-alkyl, CHO or $C_1$-$C_8$-alkylcarbonyl;

oligo-$C_2$-$C_3$-alkylene oxide $C_1$-$C_{16}$-alkylbenzene ethers;

oligo-$C_2$-$C_3$-alkylene oxide mono-, di- or tristyrylphenyl ethers;

partial esters of glycerol or sorbitan with fatty acids; and ethoxylates of monofatty acid esters of sorbitan, and also mixtures of the nonionic surfactants mentioned hereinabove.

Nonionic surfactants which are particularly preferred in the context of the present invention include oligoethylene oxide $C_8$-$C_{22}$-alkyl ethers, oligoethylene oxide cooligopropylene oxide $C_8$-$C_{22}$-alkyl ethers, ethylene oxide/propylene oxide block copolymers, monofatty acid esters of sorbitan, ethoxylated sorbitan monofatty acid esters and mono-, di- or tristyrylphenol ethoxylates, and mixtures of these.

In a preferred embodiment of the invention, component OS2 of the formulations comprises at least two nonionic surfactants having different HLB values. According to a particularly preferred embodiment, the at least two nonionic surfactants are:

OS2.1: at least one surfactant having an HLB value of at most 13, in particular of 5 to 13 and specifically of 6 to 12; and OS2.2: at least one surfactant having an HLB value of more than 13, in particular of 13.5 to 18 and specifically of 14 to 17.

In the context of the present invention, the term "HLB value" ("hydrophilic-lipophilic balance") is a measure for the degree of hydrophilicity or lipophilicity of a surfactant. The HLB value can be used for predicting the surfactant properties of a molecule. According to the method of Davies (Davies, J. T., Proceedings of the International Congress of Surface Activity, 1957, 426-438), this value is calculated using the following formula:

$$HLB = 7 + m*H^h + n*H^i$$

where m represents the number of hydrophilic groups of the molecule, $H^h$ is a value which corresponds to the specific hydrophilic character of the hydrophilic groups, n represents the number of lipophilic groups of the molecule and $H^i$ is a value which corresponds to the specific hydrophilic character of the lipophilic groups.

The nonionic surfactant OS2.1 having an HLB value of at most 13 can be selected from among all the nonionic surfactants mentioned above having an HLB value of at most 13, in particular from 5 to 13 or from 6 to 12. Suitable surfactants OS2.1 comprise in particular oligo-$C_2$-$C_3$-alkylene oxide $C_8$-$C_{22}$-alkylbenzene ethers, monofatty acid esters of sorbitan, oligo-$C_2$-$C_3$-alkylene oxide mono-, di- or tristyrylphenyl ethers and compounds of the formula I:

R—[OA]$_n$-OR'  (I), in which n denotes the average number of repeat units [OA] in the range of from 2 to 20, each A in each case independently is ethanediyl, propane-1,2-diyl, butane-1,2-diyl or 2-methylpropane-1,2-diyl, R is straight-chain or branched $C_8$-$C_{24}$-alkyl or $C_8$-$C_{24}$-alkenyl, and R' is H, $C_1$-$C_8$-alkyl, CHO or $C_1$-$C_8$-alkylcarbonyl.

Preferably the at least one nonionic surfactant OS2.1 is a monofatty acid ester of sorbitan or a compound of the formula I in which n denotes the average number of repeat units [OA] in the range of from 2 to 20, each A in each case independently is ethanediyl, propane-1,2-diyl, butane-1,2-diyl or 2-methylpropane-1,2-diyl, R is straight-chain or branched $C_8$-$C_{24}$-alkyl or $C_8$-$C_{24}$-alkenyl, and R' is H, $C_1$-$C_8$-alkyl, CHO or $C_1$-$C_8$-alkylcarbonyl.

Particular preference is given to nonionic surfactants OS2.1 of the formula I selected from the group consisting of ethoxylates and ethoxylate-co-propoxylates of straight-chain or branched $C_8$-$C_{22}$-alkanols. Examples of such preferred surfactants are ethoxylates of branched $C_{13}$-alcohols commercially available under the trade names Lutensol® TO3, Lutensol® TO5 and Lutensol® TO7 (BASF), and also ethoxylate-co-propoxylates of fatty alcohols commercially available under the trade names Plurafac LF 300, Plurafac LF 401 and Plurafac LF 1200 (BASF).

The nonionic surfactant OS2.2 having an HLB value of more than 13 can be selected from among all the nonionic surfactants mentioned above having an HLB value of more than 13, in particular of 13.5 to 18 or of 14 to 17. Suitable surfactants OS2.2 comprise in particular homo- and cooligomers of $C_2$-$C_3$-alkylene oxides, oligo-$C_2$-$C_3$-alkylene oxide $C_8$-$C_{22}$-alkylbenzene ethers, oligo-$C_2$-$C_3$-alkylene oxide mono-, di- or tristyrylphenyl ethers and compounds of the formula I:

$$R\text{—}[OA]_n\text{-}OR' \qquad (I),$$

in which n denotes the average number of repeat units [OA] in the range of from 8 to 50, each A in each case independently is ethanediyl or propane-1,2-diyl, R is straight-chain or branched $C_8$-$C_{24}$-alkyl or $C_8$-$C_{24}$-alkenyl, and R' is H, $C_1$-$C_8$-alkyl, CHO or $C_1$-$C_8$-alkylcarbonyl.

Particular preference is given to surfactants OS2.2 selected from the group consisting of propylene oxide/ethylene oxide block copolymers, oligoethylene oxide tristyrylphenyl ethers and compounds of the formula I, which are ethoxylates of straight-chain or branched $C_8$-$C_{22}$-alkanols. Examples of such preferred surfactants are ethoxylates of tristyrylphenol commercially available under the tradename Soprophor® (Rhodia), in particular Soprophor® S 25 and Soprophor® S 40, or propylene oxide/ethylene oxide block copolymers commercially available under the tradename Pluronic® PE (BASF), in particular Pluronic® PE 6200 and Pluronic® PE 6400, or ethoxylates of branched $C_{13}$-alcohols commercially available under the tradename Lutensol® (BASF), in particular Lutensol® TO15.

The anionic surfactants OS1 suitable according to the invention include in particular the sodium, potassium, calcium and ammonium salts of $C_6$-$C_{22}$-alkylsulfonates, such as, for example, laurylsulfonate and isotridecylsulfonate;

$C_6$-$C_{22}$-alkyl sulfates such as, for example, lauryl sulfate, isotridecyl sulfate, cetyl sulfate and stearyl sulfate;

arylsulfonates, in particular $C_1$-$C_{16}$-alkylbenzenesulfonates, such as, for example, cumylsulfonate, octylbenzenesulfonate, nonylbenzenesulfonate and dodecylbenzenesulfonate, naphthylsulfonate, mono- and di-$C_1$-$C_{16}$-alkylnaphthylsulfonates, such as, for example, dibutylnaphthylsulfonate;

mono- and di-$C_1$-$C_{16}$-alkyldiphenyl ether (di)sulfonates, such as, for example, dodecyldiphenyl ether disulfonate;

sulfates and sulfonates of fatty acids and fatty acid esters;

oligo-$C_2$-$C_3$-alkylene oxide $C_8$-$C_{22}$-alkyl ether sulfates, in particular sulfates of the ethoxylates of $C_8$-$C_{22}$-alkanols, such as, for example, sulfates of the ethoxylates of lauryl alcohol;

oligo-$C_2$-$C_3$-alkylene oxide $C_1$-$C_{16}$-alkylbenzene ether sulfates, in particular sulfates of the ethoxylates of $C_1$-$C_{16}$-alkylphenols;

di-$C_4$-$C_{18}$-alkyl esters of sulfosuccinic acids (or: $C_4$-$C_{18}$-dialkyl sulfosuccinates), such as, for example dioctyl sulfosuccinate;

condensates of naphthalenesulfonic acid, $C_1$-$C_{16}$-alkylnaphthalenesulfonic acid or phenolsulfonic acid with formaldehyde (or: $C_1$-$C_{16}$-naphthalenesulfonate/-formaldehyde condensates, $C_1$-$C_{16}$-alkylnaphthalenesulfonate/formaldehyde condensates and phenolsulfonate/formaldehyde condensates);

oligo-$C_2$-$C_3$-alkylene oxide mono-, di- and tristyrylphenyl ether sulfates, in particular ethoxylates of mono-, di- and tristyrylphenol;

mono- and di-$C_8$-$C_{22}$-alkyl sulfates;

oligo-$C_2$-$C_3$-alkylene oxide $C_8$-$C_{22}$-alkyl ether phosphates;

oligo-$C_2$-$C_3$-alkylene oxide $C_1$-$C_{16}$-alkylbenzene ether phosphates;

oligo-$C_2$-$C_3$-alkylene oxide mono-, di- and tristyrylphenyl ether phosphates;

oligoethylene oxide polycarboxylates, in particular homo- and cooligomers of monoethylenically unsaturated mono- or dicarboxylic acids having from 3 to 8 carbon atoms, where the cooligomers additionally have oligoethylene oxide side chains;

fatty acids, such as, for example, stearic acid; and polyphosphates, such as, for example, hexametaphosphates and triphosphates (or tripolyphosphates);

and their mixtures.

From among the anionic surfactants mentioned above, preference is given to the sodium, potassium, calcium and ammonium salts of the following:

$C_1$-$C_{16}$-alkylbenzenesulfonates;

$C_1$-$C_{16}$-alkylnaphthalenesulfonates;

oligo-$C_2$-$C_3$-alkylene oxide $C_5$-$C_{22}$-alkyl ether sulfates;

oligo-$C_2$-$C_3$-alkylene oxide $C_8$-$C_{22}$-alkyl ether phosphates;

oligo-$C_2$-$C_3$-alkylene oxide $C_1$-$C_{16}$-alkylbenzene ether sulfates;

oligo-$C_2$-$C_3$-alkylene oxide $C_1$-$C_{16}$-alkylbenzene ether phosphates;

$C_8$-$C_{22}$-alkyl sulfates;

$C_4$-$C_{18}$-dialkyl sulfosuccinates;

oligo-$C_2$-$C_3$-alkylene oxide mono-, di- and tristyrylphenyl ether sulfates;

oligo-$C_2$-$C_3$-alkylene oxide mono-, di- and tristyrylphenyl ether phosphates;

oligoethylene oxide polycarboxylates; and polyphosphates; and also mixtures thereof.

Particularly preferred anionic surfactants OS1 comprise the salts, in particular the sodium, potassium, calcium and ammonium salts, of the $C_1$-$C_{16}$-alkylbenzenesulfonates, the oligo-$C_2$-$C_3$-alkylene oxide mono-, di- and tristyrylphenyl ether sulfates, the $C_4$-$C_{18}$-dialkyl sulfosuccinates and the oligo-$C_2$-$C_3$-alkylene oxide $C_8$-$C_{22}$-alkyl ether phosphates. Examples of such preferred surfactants are dodecylbenzenesulfonate, which is available under the tradename Wettol® EM1 (BASF), ethoxylated di- and tristyrylphenol sulfate having 15 or 16 ethoxyl units, which is commercially available under the trade-names Soprophor DSS 15 and Soprophor 4D 384 (Rhodia), respectively, dioctyl sulfosuccinate, which is available under the tradename Lutensit A-BO, and the commercial product Lutensit® A-EP (BASF), which is acidic phosphoric esters of alkoxylated $C_{13}$-and $C_{15}$-fatty alcohols having 18-20 alkylene oxide groups (ratio of ethoxyl and propoxyl units about 2:1).

The weight ratio of anionic surfactants OS1 and nonionic surfactants OS2 in the formulations according to the invention is preferably in the range of from 0.1:1 to 10:1, and particularly preferably in the range of from 0.25:1 to 4:1.

According to a preferred embodiment, the formulations according to the invention comprise three surfactants which are preferably either two anionic substances OS1 and one nonionic substance OS2 or two nonionic substances OS2 and one anionic substance OS1. In the latter case, the presence of two substances OS2, these are preferably substances having different HLB values, in particular a substance OS2.1 having an HLB value of at most 13 and at least one nonionic substance OS2.2 having an HLB value of more than 13.

The total amount of surfactants OS1 and OS2 comprised in the formulations of the invention depends in general on the amounts of pyraclostrobin, optional further active compounds for crop protection and solvents LM1 and LM2, and their properties. The weight ratio of the total amount of surfactants to the total amount of active compounds for crop protection including the pyraclostrobins is usually in the range of from 0.3:1 to 30:1, preferably in the range of from 0.5:1 to 20:1, and in particular in the range of from 1:1 to 7:1. Based on the total weight of the undiluted formulations, the proportion of surfactants is in general from 5 to 55% by weight, preferably from 10 to 50% by weight and in particular from 12 to 45% by weight.

Based on the total weight of the undiluted formulations, the proportion of anionic surfactants OS1 is generally from 0.5 to 30% by weight, preferably from 1 to 25% by weight and in particular from 6 to 22.5% by weight.

Based on the total weight of the undiluted formulations, the proportion of nonionic surfactants OS2 is generally from 0.5 to 30% by weight, preferably from 1 to 25% by weight and in particular from 6 to 22.5% by weight.

The total amount of surfactants OS1 and OS2 and solvents LM1 and LM2 (=organic solvents) comprised in the formulations of the invention depends generally on the amount of pyraclostrobin used and on the type and amount of optional further organic active compounds for crop protection. The weight ratio of surfactants OS1 and OS2 plus organic solvents LM1 and LM2 to active compounds for crop protection including the pyraclostrobin is usually in the range of from 50:1 to 0.5:1, preferably in the range of from 30:1 to 1:1, and in particular in the range of from 15:1 to 2:1. Based on the total weight of the undiluted formulations, the proportion of surfactants plus solvents is in general from 10 to 95% by weight, preferably from 20 to 85% by weight and in particular from 40 to 80% by weight.

The formulations according to the invention generally comprise pyraclostrobin in a concentration of from 1 to 50% by weight, frequently from 1 to 40% by weight, in particular from 2 to 25% by weight or from 5 to 20% by weight, based on the total weight of the formulation. In the case of one or more further active compounds for crop protection in addition to pyraclostrobin, the total concentration of the active compounds for crop protection is generally in the range from 1 to 50% by weight, frequently in the range from 1 to 50% by weight and in particular in the range from 2 to 25% by weight or in the range from 5 to 20% by weight, based on the total weight of the formulation.

The formulations according to the invention also comprise water. As regards the total weight of the undiluted formulation, the amount of water is, as a rule, in the range of from 1 to 80% by weight, frequently in the range of from 5 to 50% by weight, in particular in the range of from 10 to 40% by weight and preferably in the range of from 15 to 30% by weight. It is obvious that the amount of water and the amounts of the remaining constituents total 100% by weight.

In a preferred embodiment of the invention, the formulations according to the invention comprise:
a) from 1 to 50% by weight, frequently from 1 to 40% by weight, in particular from 2 to 25% by weight or 5 to 20% by weight of pyraclostrobin;
b) from 0.5 to 40% by weight, frequently from 3 to 30% by weight, in particular from 5 to 20% by weight of at least one solvent LM1 as defined above, in particular at least one of the solvents LM1 specified as preferred or particularly preferred;
c) from 1 to 60% by weight, frequently from 5 to 35% by weight, in particular from 10 to 30% by weight of at least one solvent LM2 as defined above, in particular at least one of the solvents LM2 specified as preferred or particularly preferred;
d) from 0.5 to 30% by weight, frequently from 0.5 to 27.5% by weight or 1 to 25% by weight, in particular from 6 to 22.5% by weight of at least one anionic surfactant OS1 as defined above, in particular at least one of the sufactants OS1 specified as preferred or particularly preferred;
e) from 0.5 to 30% by weight, frequently from 0.5 to 27.5% by weight or 1 to 25% by weight, in particular from 6 to 22.5% by weight of at least one nonionic surfactant OS2 as defined above, in particular at least one of the sufactants OS2 specified as preferred or particularly preferred; and
f) water to 100% by weight, for example in an amount in the range of from 1 to 80% by weight, frequently in the range of from 5 to 50% by weight, in particular in the range of from 10 to 40% by weight and especially in the range of from 15 to 30% by weight.

The % by weight stated are in each case based on the total weight of the formulation according to the invention.

With respect to the ratios of the components a)–e), in particular with respect to the total amount of surfactants d)+e), with respect to the total amount of solvents b)+c), with respect to the total amount of surfactants d)+e) plus solvents b)+c), with respect to the ratio of the total amount of surfactants d)+e) to pyraclostrobin plus possible further active components for crop protection, with respect to the ratio of the total amount of surfactants d)+e) to the total amount of solvents b)+c) and also with respect to the ratio of the total amount of surfactants d)+e) plus solvents b)+c) to pyraclostrobin plus possible further active components for crop protection, what has been said above applies.

In addition to pyraclostrobin, the formulations according to the invention may comprise further active compounds for crop protection for increasing the activity and/or for broadening the application spectrum. However, in general pyraclostrobin is the only active compound or constitutes at least 80% by weight of the active compounds comprised in the formulation.

In addition, the formulations of the invention may comprise customary auxiliaries such as, for example, antifoams (defoamers), preservatives (bactericides), stabilizers, thickeners and other substances customarily used in aqueous pesticide formulations. The total amount of these auxiliaries is generally not more than 15% by weight, in particular not more than 10% by weight, of the weight of the undiluted formulation. The amount of an individual auxiliary will usually not exceed 5% by weight and in particular 3% by weight, with the exception of antifreeze agents.

Suitable antifoams comprise polysiloxanes, such as, for example, polydimethylsiloxane, long-chain alcohols, organofluorine compounds, fatty acids and their salts, and mixtures of these. Antifoams are usually employed in amounts of from 0.1 to 5 grams per liter of the formulations.

Suitable preservatives for preventing bacterial infection of the compositions according to the invention comprise formaldehyde, alkyl esters of para-hydroxybenzoic acid, sodium benzoate, 2-bromo-2-nitropropane-1,3-diol, ortho-phenylphenol, dichlorophene, benzyl alcohol hemiformal, thiazolinone and isothiazolinone derivatives such as, for example, alkylisothiazolinones and benzisothiazolinones, 5-chloro-2-methyl-4-isothiazolinone, pentachlorophenol, 2,4-dichlorobenzyl alcohol, and mixtures of these. Examples of suitable commercially available bactericidal products are Proxel® (ICI), Acticide® RS (Thor Chemie), Kathon® (Rohm & Haas) and Acticide MBS (Thor Chemie). In general, the amount of preservative will be from 0.1 to 10 grams per liter of the formulations.

Suitable stabilizers comprise, for example, UV absorbants such as, for example, cinnamic acid esters, 3,3-diphenyl-2-cyanoacrylates, hydroxyl- and/or alkoxy-substituted benzophenones, N-(hydroxyphenyl)-benzotriazoles, hydroxyphenyl-s-triazines, oxalamides and salicylates, for example UVINUL® 3000, 3008, 3040, 3048, 3049, 3050, 3030, 3035, 3039, 3088, UVINUL® MC80, and free-radical scavengers such as, for example, ascorbic acid, citric acid, sterically hindered amines (known as HALS compounds) such as, for example, UVINUL® 4049H, 4050H, 5050H and the like, and antioxidants such as vitamin E. In a preferred embodiment, the stabilizer is citric acid or ascorbic acid. Usually, the amount of stabilizer will be in the range of from 0.01 to 10 grams per liter of formulation.

Examples of thickeners (i.e. compounds which impart a modified flow behavior to the formulation, i.e. high viscosity at rest and low viscosity in the agitated state) are polysaccharides such as xanthan gum (Kelzan®, Kelco), Rhodopol® 23 (Rhone Poulenc) or Veegum® (R. T. Vanderbilt) and organic and inorganic layer minerals such as Attaclay® (Engelhardt).

Suitable antifreeze agents are, for example, $C_1$-$C_4$-alkanols such as ethanol, isopropanol, n-butanol, isobutanol, and also $C_2$-$C_6$-polyols such as glycerol, ethylene glycol, hexylene glycol and propylene glycol, and mixtures of these.

If the formulations according to the invention are used for the treatment of seed, they may comprise further customary components used in the treatment of seed, for example for dressing or coating. In addition to the components mentioned above, this includes in particular colorants and tackifiers.

Examples of colorants are both pigments, which are sparingly soluble in water, and dyes, which are soluble in water. Examples which may be mentioned are the dyes known by the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of stickers, or tackifiers and adhesives, are ethylene oxide or propylene oxide block polymer surfactants and also polyvinyl alcohols, polyvinyl acetates, partially hydrolyzed polyvinyl acetates, polyvinylpyrrolidones, polyacrylates, polymethacrylates, polybutenes, polyisobutenes, polystyrenes, polyethylenamines, polyethylenamides, polyethylenimines (Lupasol®, Polymin®), polyethers and copolymers which are derived from the abovementioned polymers.

The customary auxiliaries mentioned above can be added during the preparation of the compositions according to the invention, or alternatively during or after dilution with water in the preparation of the ready-to-use composition.

In general, the microemulsions of the present invention can be prepared by simply mixing the constituents until an apparently homogeneous liquid has formed. The order in which the constituents are added is usually of minor importance. For example, the constituents may be put into a container and the mixture thus obtained is homogenized, for example by stirring, until a homogeneous liquid has formed. However, it is also possible first to dissolve the organic active compounds for crop protection in at least one of the solvents LM1 and/or LM2, or a mixture of these solvents with at least one of the surfactants OS1 and/or OS2 and to mix the resulting solution with water and the remaining constituents, for example by adding the solution to the water, or by adding the water to the solution. The temperature during mixing and the further mixing conditions are of minor importance. Usually, mixing of the constituents is carried out at temperatures of from 10° C. to 90° C., in particular from 10° C. to 60° C. Higher temperatures, for example 35° C. or 45° C. or higher, may be expedient to accelerate the formation of the microemulsion. On the other hand, mixing can, as a rule, also be carried out at lower temperatures, approximately at 10° C. to 35° C.

Depending on the nature of the active compound for crop protection possibly additionally present in addition to pyraclostrobin, the formulations according to the invention are useful for controlling a large number of pests and can be employed both for the treatment of crops of plants and of seed and of inanimate material and for domestic purposes.

In the present context, "pests" or "harmful organisms" are understood as meaning all types of pests which can be combated or controlled using organic active compounds for crop protection, i.e. pesticides, in particular fungicides and mixtures of fungicides with other pesticides. The term pest therefore comprises phytopathogenic organisms, in particular harmful fungi and their spores, but also harmful insects, arachnids, nematodes and harmful plants. The term "control" comprises both the curative treatment, i.e. the treatment of infected plants with a formulation according to the invention, and the protective treatment, i.e. the treatment of plants for protection against infection by a pest.

The present invention therefore also relates to:
use of formulations described herein for controlling pests, in particular plant pests; and
methods of controlling harmful organisms, in particular of phytopathogenic organisms, comprising the bringing into contact of the harmful organisms, of their habitat, of their hosts, such as plants and seed, and of the soil, the area and the environment in which they grow or might grow, but also of materials, plants, seeds, soil, surfaces or spaces which are to be protected from attack by, or infection with, phytopathogenic organisms, with an effective amount of the formulations according to the invention.

A further aspect of the invention relates to the use of the formulations described herein for protecting plants, including seed, in particular for protecting useful plants against attack by harmful organisms, in particular harmful fungi. The present invention thus also relates to the use of the formulations for controlling phytopathogenic organisms such as, for example, harmful fungi, insects, arachnids, nematodes and harmful plants, in particular for controlling harmful fungi.

In crop protection, the formulations according to the invention can be employed in particular in a manner known per se as foliar fungicides, fungicides for seed dressing and soil fungicides for the control of phytopathogenic fungi.

They are of particular importance for controlling a large number of fungi on various crop plants, such as wheat, rye, barley, triticale, oats, rice, corn, grass, bananas, cotton, soybeans, coffee, sugarcane, grapevines, fruit and ornamental plants and vegetable plants, such as cucumbers, beans, tomatoes, potatoes and cucurbits, and also on the seeds of these plants.

In particular, the formulations according to the invention of pyraclostrobin in principle allow the control of all diseases caused by harmful fungi which can also be controlled with known formulations of pyraclostrobin. Depending on the respective mixing partner optionally present, these are, for example, the following plant diseases:

*Alternaria* species on vegetables, oilseed rape, sugarbeets, soybeans, cereals, cotton, fruit and rice (for example *A. solani* or *A. alternata* on potatoes and other plants),

*Aphanomyces* species on sugarbeet and vegetables,

*Ascochyta* sp. on cotton and rice,

*Bipolaris* and *Drechslera* species on corn, cereals, rice and lawn (for example *D. teres* on barley, *D. tritci*-repentis on wheat),
*Blumeria graminis* (powdery mildew) on cereals,
*Botrytis cinerea* (gray mold) on strawberries, vegetables, flowers and grapevines,
*Botryodiplodia* sp. on cotton,
*Bremia lactucae* on lettuce,
*Cercospora* species on corn, soybeans, rice and sugarbeet (for example *C. beticula* on sugarbeet),
*Cochliobolus* species on corn, cereals, rice (for example *Cochliobolus sativus* on cereals, *Cochliobolus miyabeanus* on rice),
*Corynespora* sp. on soybeans, cotton and other plants,
*Colletotrichum* species on soybeans, cotton and other plants (for example *C. acutatum* on various plants),
*Curvularia* sp. on cereals and rice,
*Diplodia* sp. on cereals and rice,
*Exserohilum* species on corn,
*Erysiphe cichoracearum* and *Sphaerotheca fuliginea* on cucumber plants,
*Fusarium* and *Verticillium* species (for example *V. dahliae*) on various plants (for example *F. graminearum* on wheat),
*Gaeumanomyces graminis* on cereals,
*Gibberella* species on cereals and rice (for example *Gibberella fujikuroi* on rice),
Grainstaining complex on rice,
*Helminthosporium* species (for example *H. graminicola*) on corn and rice,
*Macrophomina* sp. on soybeans and cotton,
*Michrodochium* sp. (for example *M. nivale* on cereals),
*Mycosphaerella* species on cereals, bananas and peanuts (*M. graminicola* on wheat, *M. fijiesis* on bananas),
*Phaeoisaripsis* sp. on soybeans,
*Phakopsara* sp. (for example *P. pachyrhizi* and *P. meibomiae* on soybeans),
*Phoma* sp. on soybeans,
*Phomopsis* species on soybeans, sunflowers and grape-vines (*P. viticola* on grape-vines, *P. helianthii* on sunflowers),
*Phytophthora infestans* on potatoes and tomatoes,
*Plasmopara viticola* on grapevines,
*Penecilium* sp. on soybeans and cotton,
*Podosphaera leucotricha* on apples,
*Pseudocercosporella herpotrichoides* on cereals,
*Pseudoperonospora* species on hops and cucumber plants (for example *P. cubenis* on cucumber),
*Puccinia* species on cereals, corn and asparagus (*P. triticina* and *P. striformis* on wheat, *P. asparagi* on asparagus),
*Pyrenophora* species on cereals,
*Pyricularia oryzae, Corticium sasakii, Sarocladium oryzae, S. attenuatum, Entyloma oryzae* on rice,
*Pyricularia grisea* on lawn and cereals,
*Pythium* spp. on lawn, rice, corn, cotton, oilseed rape, sunflowers, sugarbeet, vegetables and other plants,
*Rhizoctonia* species (for example *R. solani*) on cotton, rice, potatoes, lawn, corn, oilseed rape, potatoes, sugarbeet, vegetables and other plants,
*Rynchosporium* sp. (for example *R. secalis*) on rice and cereals,
*Sclerotinia* species (for example *S. sclerotiorum*) on oilseed rape, sunflowers and other plants,
*Septoria tritici* and *Stagonospora nodorum* on wheat,
*Erysiphe* (syn. *Uncinula necator*) on grapevines,
*Setospaeria* species on corn and lawn,
*Sphacelotheca reilinia* on corn,
*Thievaliopsis* species on soybeans and cotton,
*Tilletia* species on cereals,
*Ustilago* species on cereals, corn and sugarbeet, and
*Venturia* species (scab) on apples and pears (for example *V. inaequalis* on apples).

The formulations according to the invention can be used together with formulations of other active compounds for crop protection for increasing the activity and/or for broadening the application spectrum. Here, the term "active compound for crop protection" is to be interpreted widely and comprises substances protecting plants against attack by harmful organisms, substances which kill plant-damaging organisms or prevent their development and substances which have an effect on the growth of the useful plant, i.e. enhance or reduce growth, including substances which serve to improve plant health. The active compounds for crop protection include, for example:

fungicides, i.e. active compounds which kill phytopathogenic fungi or prevent their growth or reduce the infection of the useful plant with such phytopathogenic fungi;

insecticides, acaricides and nematicides, i.e. active compounds which kill plant-damaging arthropods or nematodes or impede their development in a manner such that an infestation of the useful plant is prevented effectively or the infestation of a plant with these harmful organisms is reduced;

herbicides, i.e. active compounds which kill harmful plants or reduce or prevent their growth;

growth regulators, i.e. active compounds which promote or reduce plant growth;

safeners, i.e. active compounds which reduce or prevent a phytotoxic effect caused by the substances mentioned above on the useful plant; and also fertilizers.

Suitable active compounds for crop protection are known, for example, from W. Krämer and U. Schirmer (ed.) "Modern Crop Protection Compounds" Vol. 2, Wiley-VHC 2007; C. D. S. Tomlin, "The Pesticide Manual", 13th Edition, British Crop Protection Council (2003); and from "The Compendium of Pesticide Common Names", http://www.alanwood.net/pesticides/.

Suitable active compounds for crop protection which are optionally, applied with the formulations according to the invention are in particular those typically employed together with pyraclostrobin.

Typical fungicidal mixing partners of pyraclostrobin are, for example:

acylalanines, such as benalaxyl, metalaxyl, ofurace, oxadixyl, amine derivatives such as aldimorph, dodine, dodemorph, fenpropimorph, fenpropidin, guazatine, iminoctadine, spiroxamine, tridemorph, anilinopyrimidines, such as pyrimethanil, mepanipyrim or cyprodinil, antibiotics, such as cycloheximide, griseofulvin, kasugamycin, natamycin, polyoxin or streptomycin, azoles, such as bitertanol, bromoconazole, cyproconazole, difenoconazole, dinioconazole, epoxiconazole, fenbuconazole, fluquinconazole, flusilazole, hexaconazole, imazalil, metconazole, myclobutanil, penconazole, propiconazole, prochloraz, prothioconazole, tebuconazole, triadimefon, triadimenol, triflumizole, triticonazole, dicarboximides, such as iprodione, myclozolin, procymidone, vinclozolin, dithiocarbamates, such as ferbam, nabam, maneb, mancozeb, metam, metiram, propineb, polycarbamate, thiram, ziram, zineb, heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, thiophanate-ethyl, tiadinil, tricyclazole, triforine, nitrophenyl derivatives, such as binapacryl, dinocap, dinobuton, nitrophthal-isopropyl, phenylpyrroles, such as fenpiclonil or fludioxonil, sulfur, other fungicides, such as acibenzolar-S-methyl, benthiavalicarb, carpropamid, chlorothalonil, cymoxanil, diclomezine, diclocymet, diethofencarb, edifenphos, ethaboxam, fenhexamid, fentin acetate, fenoxanil, ferimzone, fluazinam, fosetyl, fosetyl-aluminum, iprovalicarb, hexachlorobenzene, metrafenone, pencycuron, propamocarb, phthalide, toloclofos-methyl, quintozene, zoxamide, sulfenic acid derivatives, such as captafol, captan, dichlofluanid, folpet, tolylfluanid, cinnamides and analogs, such as dimethomorph, flumetover or flumorph, 6-aryl[1,2,4]triazolo[1,5-a]pyrimidines as described, for example, in WO 98/46608, WO 99/41255 or WO 03/004465, in each case by the general formula I, amide fungicides, such as cyflufenamid, and also (Z)-N-[α-(cyclopropylmethoxyimino)-2,3-difluoro-6-(difluoromethoxy)benzyl]-2-phenylacetamide.

Preferred fungicidal mixing partners of pyraclostrobin are: metalaxyl, dodemorph, fenpropimorph, fenpropidin, guazatine, spiroxamine, tridemorph, pyrimethanil, cyprodinil, bitertanol, bromoconazole, cyproconazole, difenoconazole, dinitroconazole, epoxiconazole, fenbuconazole, fluquinconazole, flusilazole, hexaconazole, imazalil, metconazole, myclobutanil, penconazole, propiconazole, prochloraz, prothioconazole, tebuconazole, triadimefon, triadimenol, triflumizole, triticonazole, iprodione, vinclozolin, maneb, mancozeb, metiram, thiram, boscalid, carbendazim, carboxin, oxycarboxin, cyazofamid, dithianon, famoxadone, fenamidone, fenarimol, flutolanil, quinoxyfen, thiophanate-methyl, thiophanate-ethyl, triforine, dinocap, nitrophthal-isopropyl, phenylpyr-roles, such as fenpiclonil or fludioxonil, acibenzolar-S-methyl, benthiavalicarb, carpropamid, chlorothalonil, cyflufenamid, cymoxanil, fenhexamid, fentinacetate, fenoxanil, fluazinam, fosetyl, fosetyl-aluminum, iprovalicarb, metrafenone, zoxamide, captan, folpet, dimethomorph, azoxystrobin, dimoxystrobin, fluoxastrobin, kresoxim-methyl, metominostrobin, orysastrobin, picoxystrobin or trifloxystrobin.

Particularly preferred fungicidal mixing partners are metalaxyl, fenpropimorph, fenpropidin, guazatine, spiroxamine, pyrimethanil, cyprodinil, cyproconazole, difenoconazole, epoxiconazole, fenbuconazole, fluquinconazole, flusilazole, hexaconazole, metconazole, myclobutanil, propiconazole, prochloraz, prothioconazole, tebuconazole, triticonazole, iprodione, vinclozolin, boscalid, carbendazim, carboxin, oxycarboxin, cyazofamid, dithianon, quinoxyfen, thiophanate-methyl, thiophanate-ethyl, dinocap, nitrophthal-isopropyl, fenpiclonil or fludioxonil, benthiavalicarb, carpropamid, fenhexamid, fenoxanil, fluazinam, iprovalicarb, metrafenone, zoxamide, dimethomorph, azoxystrobin, dimoxystrobin, fluoxastrobin, kresoxim-methyl, metominostrobin, orysastrobin, picoxystrobin or trifloxystrobin.

Very particularly preferred fungicidal mixing partners are fenpropimorph, cyproconazole, difenoconazole, epoxiconazole, fenbuconazole, fluquinconazole, flusilazole, hexaconazole, metconazole, myclobutanil, propiconazole, prochloraz, prothioconazole, tebuconazole, triticonazole, boscalid, dithianon, quinoxyfen, thiophanate-methyl, thiophanate-ethyl, dinocap, fenpiclonil or fludioxonil, benthiavalicarb, carpropamid, fenhexamid, fenoxanil, fluazinam, iprovalicarb, metrafenone, zoxamide, dimethomorph, azoxystrobin, dimoxystrobin, fluoxastrobin, kresoxim-methyl, metominostrobin, orysastrobin, picoxystrobin or trifloxystrobin.

The formulations according to the invention can also be applied together with insecticidally, acaricidally or nematicidally active compounds. In particular, it has been found to be advantageous to employ pyraclostrobin together with at least one active compound which acts against stinging, chewing, biting or sucking insects and other arthropods, for example from the order of the Coleoptera, in particular *Phyllophaga* sp., such as *Phyllophaga cuyabana*, *Sternechus* sp., such as *Sternechus pingusi*, *Sternechuns subsignatus*, *Promecops* sp. such as *Promecops carinicollis*, *Aracanthus* sp. such as *Aracanthus morei*, and *Diabrotica* sp. such as *Diabrotica speciosa*, *Diabrotica longicornis*, *Diabrotica* 12-punctata, *Diabrotica virgifera*, *Oryzophagus* sp., Lepidoptera, in particular *Elasmopalpus* sp. such as *Elasmopalpus lignosellus*, *Diloboderus* sp., Isoptera, in particular *Rhinotermitida*, Homoptera, in particular *Dalbulus maidis*, or against nematodes, including root-knot nematodes, for example *Meloidogyne* spp., such as *Meloidogyne hapla*, *Meloidogyne incognita*, *Meloidogyne javanica*, and other *Meloidogyne* species; cyst-forming nematodes, such as *Globodera rostochiensis* and other *Globodera* species; *Heterodera avenae*, *Heterodera glycines*, *Heterodera schachtii*, *Heterodera trifolii*, and other *Heterodera* species; gall nematodes, for example *Anguina* species; stem eelworms and foliar nematodes, such as *Aphelenchoides* species.

A formulation according to the invention together with a formulation which comprises thiophanate-methyl or -ethyl, for example, can be used for controlling the following harmful fungi:

*Alternaria* sp. on cereals, cotton and rice,
*Ascochyta* sp. on cotton and rice,
*Botryodiplodia* sp. on cotton,
*Cercospora* species on corn, soybeans, rice and other plants,
*Corynespora* sp. on soybeans, cotton and other plants,
*Colletotrichum* species on soybeans, cotton and other plants,
*Curvularia* sp. on cereals and rice,
*Diplodia* sp. on cereals and rice,
*Drechslera* sp. on cereals and rice,
*Fusarium* sp. on cereals, soybeans and cotton,
*Gibberella* sp. on cereals and rice,
*Macrophomia* sp. on soybeans and cotton,
*Penecilium* sp. on soybeans and cotton,
*Phaeoisaripsis* sp. on soybeans,
*Phoma* sp. on soybeans,
*Phomopsis* sp. on soybeans,
*Pythium* sp. on soybeans and cotton,
*Pyrenophora* sp.,
*Pyricularia* sp. on rice,
*Rhizoctonia* sp. on soybeans, rice and cotton,
*Rhychosporium* sp. on rice, Septoria sp. on soybeans,
Tilletia sp. on cereals and rice,
Ustilago sp. on cereals.

A formulation according to the invention together with a formulation which comprises thiophanate-methyl or -ethyl and fipronil or another GABA antagonist such as acetoprole, endosulfan, ethiprole, vaniliprole, pyrafluprole or pyriprole, for example, can be used for controlling the harmful fungi mentioned above with simultaneous control of insects, for example Coleoptera, in particular *Phyllophaga* sp., such as *Phyllophaga cuyabana*, *Sternechus* sp., such as *Sternechus pingusi*, *Sternechuns subsignatus*, *Promecops* sp., such as *Promecops carinicollis*, *Aracanthus* sp., such as *Aracanthus morei*, and *Diabrotica* sp., such as *Diabrotica speciosa*, *Diabrotica longicornis*, *Diabrotica* 12-punctata, *Diabrotica virgifera*, *Oryzophagus* sp., and Lepidoptera, in particular *Elasmopalpus* sp., such as *Elasmopalpus lignosellus*, *Diloboderus* sp.

A formulation according to the invention together with a formulation which comprises epoxyconazole, for example, can be used for controlling the following harmful fungi:
Microdochium sp. on cereals,
Tilletia sp. on cereals and rice,
Ustilago sp. on cereals.

A formulation according to the invention together with one or two formulations which comprise triticonazole and prochloraz or prochloraz-CuCl, for example, can be used for controlling the following harmful fungi:
Microdochium sp. on cereals,
Tilletia sp. on cereals and rice,
Ustilago sp. on cereals.

The formulations according to the invention can be applied in undiluted form or as a dilution with water. In general, they are diluted with at least one part of water, preferably with 10 parts of water and in particular with at least 100 parts of water, for example with 1 to 10000, preferably 100 to 5000 and particularly preferably with 500 to 2000 parts of water, based on one part of the formulation.

Dilution is usually effected by pouring the microemulsions according to the invention into the water. Usually, agitation, such as, for example, stirring, is employed for rapidly mixing the concentrate with water. However, agitation is not generally necessary. Although the temperature is not a critical factor for the dilution process, dilutions are usually carried out at temperatures in the range of from 0° C. to 50° C., in particular at 10° C. to 30° C., or at ambient temperature.

The water employed for diluting is, in general, tap water. However, the water may already comprise water-soluble compounds which are used in plant protection, such as, for example, nutrients, fertilizers or pesticides.

The microemulsions of the invention can be applied in a conventional manner, usually in the form of the aqueous dilutions described above. The required application rates of the pure active compounds without formulation auxiliaries depend on the intensity of the infestation by pests, on the development phase of the plants, on the climatic conditions at the application site and on the application method. In general, the application rate is in the range of from 0.001 to 3 kg, preferably from 0.005 to 2 kg, in particular from 0.01 to 1 kg and especially from 50 to 500 g of active compound per hectare, active compound here being pyraclostrobin plus optional further active compounds.

The formulations of the invention, which are generally diluted, are applied mainly by spraying, in particular spraying of the leaves. Application can be carried out using spraying techniques known to the person skilled in the art, for example using water as carrier and amounts of spray liquor of about 100 to 1000 liters per hectare, for example from 300 to 400 liters per hectare.

A further aspect of the invention relates to seed treatment. The term seed treatment comprises all suitable methods known to the person skilled in the art for treating seed, such as, for example, seed dressing, seed coating, seed soaking, seed film coating, seed multilayer coating, seed encrusting, seed dripping, seed dusting and seed pelleting.

According to a first embodiment of seed treatment, the seed, i.e. the plant parts capable of propagation, intended for sowing, is treated with a formulation according to the invention or an aqueous dilution thereof. Here, the term seed comprises seeds and plant parts capable of propagation of any type, including seeds, seed grains, parts of seeds, saplings, fruits, tubers, cereal grains, cuttings and the like, in particular grains and seeds.

Alternatively, the seed may also be treated with the plant protection formulation according to the invention during sowing. In a further embodiment of the seed treatment or soil treatment according to the invention, the furrows are treated with the formulation according to the invention either before or after sowing of the seed.

The seed which has been treated in accordance with the invention is distinguished by advantageous properties in comparison with conventionally treated seed and therefore also forms part of the subject matter of the present application.

According to a further aspect of the invention, it is possible to treat plants, seed or soils preventatively with the formulations, for example to guard against attack by pests or to prevent an expected attack by pests.

In general, the type and nature of the application of a formulation according to the invention should depend on the respective intended purpose; in each case, it should ensure the finest possible distribution of the active compounds for crop protection comprised in the formulation.

The novel pyraclostrobin-comprising crop protection formulations have advantageous properties for the treatment of plants and seed; in particular, they have good application properties, high stability and high fungicidal activity.

The examples below serve to illustrate the invention.

I. Preparation of Formulations (General Protocol)

The ingredients listed in Table 1 were employed.

TABLE 1

Ingredients of groups A to E for the formulations listed in Table 2.

| A* | B* | C** | D | E |
|---|---|---|---|---|
| γ-butyrolactone (miscible) | acetophenone (5.5 g/l) | Solvesso ® 150 ND | emulsifiers 1, 2, 3, 4, 5 and 6 | emulsifiers 15, 16, 17 and 18 |
| propylene glycol (miscible) | benzyl alcohol (39 g/l) | Solvesso ® 200 ND | emulsifier 9 | |
| hexylene glycol | cyclohexanone | Agnique ® | emulsifiers 10, | |

TABLE 1-continued

Ingredients of groups A to E for the formulations listed in Table 2.

| A* | B* | C** | D | E |
|---|---|---|---|---|
| (miscible) Purasolv ® NPL (n-propyl lactate) (miscible) DMSO (miscible) | (24 g/l) 2-heptanone (4.3 g/l) | KE 3658 Edenor ® TI 05 | 11, 12, 13 and 14 | |

*The solubility of the respective solvent in water at 20° C. is indicated in brackets. The term 'miscible' means complete miscibility with water.
**All solvents of the group C have a solubility in water of less than 0.1 g/l at 20° C.
A: organic solvents having a solubility in water of at least 200 g/l at 20° C. (correspond to solvents LM2.1 of the formulations of the invention);
B: organic solvents having a solubility in water of from 2 to 200 g/l at 20° C. (correspond to solvents LM2.2 of the formulations of the invention);
C: organic solvents having a solubitlity in water of less than 2 g/l at 20° C. (correspond to solvents LM1 of the formulations of the invention);
D: nonionic surfactants (correspond to component e) of the formulations of the invention);
E: anionic surfactants (correspond to component d) of the formulations of the invention).

Explanation of Trade Names:
Edenor® TI 05: Fatty acid mixture with a high oleic acid content (Cognis),
Agnique® KE 3658: Fatty acid dimethyl amides (Cognis);
Solvesso® 150 ND: Predominantly $C_{10}$- and $C_{11}$-alkylbenzenes with a boiling range of from 175 to 209° C., naphthalene-depleted (ExxonMobil Chemical);
Solvesso® 200 ND: Predominantly $C_{10}$- and $C_{14}$-alkylnaphthalenes with a boiling range of from 235 to 305° C., naphthalene-depleted (ExxonMobil Chemical);
emulsifier 1: C13-oxoalcohol oligoethoxylate having 5 ethylene oxide (EO) units, HLB value: 10.5;
emulsifier 2: C13-oxoalcohol oligoethoxylate having 10 EO units, HLB value: 13.5;
emulsifier 3: C13-oxoalcohol oligoethoxylate having 11 EO units, HLB value: 14.0;
emulsifier 4: C13-oxoalcohol oligoethoxylate having 15 EO units, HLB value: 15.5;
emulsifier 5: 2-propylheptanol oligoethoxylate having 5 EO units, HLB value: 11.5;
emulsifier 6: 2-propylheptanol oligoethoxylate having 14 EO units, HLB value: 16.0;
emulsifier 7: C10-oxoalcohol oligoethoxylate having 7 EO units, HLB value: 13.0;
emulsifier 8: tristyrylphenol oligoethoxylate having 25 EO units, HLB value: 14.5 (Soprophor® S 25, Rhodia);
emulsifier 9: sorbitan monofatty acid ester (mainly monododecanoate), HLB value: 8.0;
emulsifier 10: ethoxylated sorbitan monolaurate having about 20 EO units, HLB value: 16.7;
emulsifier 11: fatty alcohol alkoxylate (Plurafac LF 300, BASF);
emulsifier 12: fatty alcohol alkoxylate (Plurafac LF 401, BASF);
emulsifier 13: fatty alcohol alkoxylate (Plurafac LF 1200, BASF);
emulsifier 14: propylene oxide/ethylene oxide block polymer comprising about 40% EO (Pluronic PE 6400, BASF);
emulsifier 15: sodium 2-sulfonyldioctyl succinate;
emulsifier 16: acidic phosphoric ester of alkoxylated $C_{13}$/$C_{15}$-fatty alcohols having 18-20 alkylene oxide groups (ethylene oxide/propylene oxide ratio about 2:1);
emulsifier 17: ethoxylated distyrylphenol sulfate having 15 EO units (Soprophor® DSS 15, Rhodia);
emulsifier 18: ethoxylated tristyrylphenol ammoniumsulfate having 16 EO units (Soprophor® 4D 384, Rhodia).

Formulations 1 to 44 are listed in Table 2. Table 2 also shows the ingredients and their amounts used for preparing the respective formulations. The preparation was carried out as described below, where all steps were carried out at room temperature (RT): pyraclostrobin and optionally further active compounds were initially charged in a container, and after addition of three or more components A, B and C (cf. Table 1) the mixture was stirred until the pyraclostrobin had been dissolved as completely as possible. With careful stirring, two or more components D and E (cf. Table 1) were then added, and stirring was continued until a solution as homogeneous as possible was obtained. Thereafter, the distilled water was added, with stirring, and the mixture was stirred until a clear formulation was obtained.

II. Stability Tests of the Formulations

The formulations prepared were examined for their stability at low and high temperatures and also after dilution with water. In each case, their macroscopic appearance was then examined. A homogeneous and clear liquid indicated a microemulsion which had remained stable, whereas opaque, turbid, highly turbid and two-phase mixtures indicated, in this order, increasing droplet size or phase separation. Here, the transition from turbid to highly turbid, milky appearance corresponded approximately to the transition from microemulsion to conventional emulsion. In one case, freezing of the sample was also observed at low temperature.

Dilution tests: The formulations were in each case diluted with 100 parts of water and allowed to stand for 2 hours, and their macroscopic appearance was then examined as described above. As shown in an exemplary manner in Table 3, over a period of 24 hours none of the exemplary formulations showed formation of a sediment.

Temperature tests: The formulations were stored at −10° C. or 54° C. for 14 days, and their macroscopic appearance was then examined. The results of these stability tests are likewise shown in an exemplary manner in Table 3.

The abbreviations used in Table 3 are to be understood as follows:

| | |
|---|---|
| ch | clear, homogeneous |
| oh | opaque, homogeneous |
| th | turbid, homogeneous |
| e | highly turbid emulsion |
| solid | homogeneous solid (frozen) |

III. Tests With Regard to Fungicidal Action

For the tests below, the formulations according to the invention were diluted with water to concentrations of 200, 400 and 600 ppm and 63, 250 and 1000 ppm, respectively (with respect to active compound content). For comparative purposes, an EC (emulsion concentrate) formulation (standard formulation) in accordance with the prior art comprising solvents, pyraclostrobin and surfactants was diluted with water to the given concentrations.

6 to 7 days after sowing, leaves of wheat seedlings of the cultivar "Kanzler" were inoculated with a spore suspension of brown rust (*Puccinia recondita*). 48 hours after the inoculation, the infected plants were sprayed with the aqueous active compound preparations described above at the stated active compound concentrations (200 l/ha). 8 days after this treatment, the extent of the rust fungus development on the leaves was determined. Each test was repeated three times, and the mean of the plant infection was calculated. The results of these tests for a selection of formulations according to the invention are shown in Table 4. In the table, the fungicidal activity is stated as the quotient EW/EC of infection after treatment with the respective exemplary formulation EW according to the invention and infection after treatment with the EC formulation mentioned. Thus, 1 denotes an activity comparable to that of the EC formulation, values of less than 1 indicate an activity better than that of the EC formulation and 0 indicates no infection.

TABLE 2

Formulations (the numeric values are amounts in gram)

| Example | 1 | 2 | 3 | 4 | 5 | 6 | 7 | 8 |
|---|---|---|---|---|---|---|---|---|
| pyraclostrobin | 100.0 | 100.0 | 100.0 | 100.0 | 125.0 | 100.0 | 100.0 | 125.0 |
| Solvesso 200 ND | | | 175.0 | 175.0 | 108.0 | 175.0 | 175.0 | 108.0 |
| Solvesso 150 ND | 175.0 | 175.0 | | | | | | |
| benzyl alcohol | | | 175.0 | | | 175.0 | 175.0 | |
| acetophenone | 175.0 | 175.0 | | | 108.0 | | | 108.0 |
| γ-butyrolactone | | | | | 108.0 | | | 108.0 |
| Purasolv NPL | | | | 175.0 | | | | |
| emulsifier 15 | 72.0 | | | 72.0 | 44.0 | | | |
| emulsifier 18 | | 108.0 | 108.0 | | | | | 88.0 |
| emulsifier 17 | | | | | | 108.0 | 108.0 | |
| emulsifier 1 | | 36.0 | 36.0 | | 44.0 | 36.0 | | 132.0 |
| emulsifier 5 | | | | | | — | 36.0 | |
| emulsifier 9 | | | | | | — | | |
| emulsifier 3 | | | | | 132.0 | | | |
| emulsifier 4 | 108.0 | 36.0 | 36.0 | | | | | |
| emulsifier 6 | | | | | | | 36.0 | |
| emulsifier 10 | | | | | | | | |
| emulsifier 8 | | | | 108.0 | | 36.0 | | |
| hexylene glycol | 150.0 | 150.0 | 150.0 | 150.0 | 130.0 | 150.0 | 150.0 | 130.0 |
| propylene glycol | | | | | | | | |
| deionized water | 220.0 | 220.0 | 220.0 | 220.0 | 220.0 | 220.0 | 220.0 | 220.0 |
| total | 1000.0 | 1000.0 | 1000.0 | 1000.0 | 1019.0 | 1000.0 | 1000.0 | 1019.0 |

| Example | 9 | 10 | 11 | 12 | 13 |
|---|---|---|---|---|---|
| pyraclostrobin | 125.0 | 100.0 | 100.0 | 100.0 | 100.0 |
| Solvesso 200 ND | 108.0 | 175.0 | 175.0 | 175.0 | |
| Solvesso 150 ND | | | | | 175.0 |
| benzyl alcohol | | 175.0 | 175.0 | 175.0 | |
| acetophenone | 108.0 | | | | 175.0 |
| γ-butyrolactone | 108.0 | | | | |
| Purasolv NPL | | | | | |
| emulsifier 15 | | | | | 72.0 |
| emulsifier 18 | 132.0 | 108.0 | 108.0 | 108.0 | |
| emulsifier 17 | | | | | |
| emulsifier 1 | 44.0 | | | | |
| emulsifier 5 | | | 36.0 | | |
| emulsifier 9 | | 72.0 | | | |
| emulsifier 3 | 44.0 | | | | |
| emulsifier 4 | | | | | |
| emulsifier 6 | | | 36.0 | | |
| emulsifier 10 | | | | 72.0 | |
| emulsifier 8 | | | | | 108.0 |
| hexylene glycol | 130.0 | 150.0 | 150.0 | 150.0 | 150.0 |
| propylene glycol | | | | | |
| deionized water | 220.0 | 220.0 | 220.0 | 220.0 | 220.0 |
| total | 1019.0 | 1000.0 | 1000.0 | 1000.0 | 1000.0 |

| Example | 14 | 15 | 16 | 17 | 18 | 19 | 20 | 21 |
|---|---|---|---|---|---|---|---|---|
| pyraclostrobin | 125.0 | 125.0 | 125.0 | 125.0 | 150.0 | 150.0 | 125.0 | 150.0 |
| Solvesso 200 ND | 162.5 | 162.5 | 162.5 | 162.5 | 180.0 | 180.0 | 162.5 | 180.0 |
| Solvesso 150 ND | | | | | | | | |
| benzyl alcohol | 162.5 | 162.5 | 162.5 | 162.5 | 120.0 | 120.0 | | |
| acetophenone | | | | | | | | |
| γ-butyrolactone | | | | | | | | |

TABLE 2-continued

Formulations (the numeric values are amounts in gram)

| | | | | | | | | |
|---|---|---|---|---|---|---|---|---|
| Purasolv NPL | | | | | | | 162.5 | 120.0 |
| emulsifier 15 | | | | | | | 88.0 | 80.0 |
| emulsifier 16 | | | | | | | | |
| emulsifier 18 | | | 132.0 | 132.0 | 120.0 | 120.0 | | |
| emulsifier 17 | 108.0 | 132.0 | | | | | | |
| emulsifier 1 | | | 88.0 | 44.0 | 80.0 | 40.0 | | |
| emulsifier 5 | 72.0 | 88.0 | | | | — | | |
| emulsifier 3 | | | | | | | | |
| emulsifier 4 | | | | 44.0 | | 40.0 | | |
| emulsifier 8 | | | | | | | 132.0 | 120.0 |
| hexylene glycol | 150.0 | 80.0 | 80.0 | 80.0 | 80.0 | 80.0 | | 80.0 |
| propylene glycol | | | | | | | | |
| deionized water | 220.0 | 250.0 | 250.0 | 250.0 | 270.0 | 270.0 | 330.0 | 270.0 |
| total | 1000.0 | 1000.0 | 1000.0 | 1000.0 | 1000.0 | 1000.0 | 1000.0 | 1000.0 |

| Example | 22 | 23 | 24 | 25 | 26 | 27 | 28 | 29 |
|---|---|---|---|---|---|---|---|---|
| pyraclostrobin | 125.0 | 125.0 | 125.0 | 125.0 | 125.0 | 125.0 | 125.0 | 125.0 |
| Solvesso 200 ND | 108.0 | 108.0 | 108.0 | 108.0 | 115.0 | 115.0 | 115.0 | 115.0 |
| Solvesso 150 ND | | | | | | | | |
| benzyl alcohol | | | | | | | | |
| acetophenone | 108.0 | 108.0 | 108.0 | 108.0 | 110.0 | 110.0 | 110.0 | 110.0 |
| γ-butyrolactone | 108.0 | | 108.0 | | 100.0 | 100.0 | 100.0 | 100.0 |
| Purasolv NPL | | 108.0 | | 108.0 | | | | |
| emulsifier 15 | | 220.0 | 88.0 | | | | | |
| emulsifier 16 | | | | | | | | |
| emulsifier 18 | 220.0 | | | 176.0 | 176.0 | 121.0 | 110.0 | 121.0 |
| emulsifier 17 | | | | | | | | |
| emulsifier 1 | | | 132.0 | | 22.0 | 66.0 | 66.0 | 44.0 |
| emulsifier 5 | | | | | | | | |
| emulsifier 3 | | | | | 11.0 | 16.5 | 22.0 | 27.5 |
| emulsifier 4 | | | | 44.0 | 11.0 | 16.5 | 22.0 | 27.5 |
| emulsifier 8 | | | | | | | | |
| hexylene glycol | 130.0 | 130.0 | 130.0 | 130.0 | 130.0 | 130.0 | | |
| propylene glycol | | | | | | | 130.0 | 130.0 |
| deionized water | 220.0 | 220.0 | 220.0 | 220.0 | 220.0 | 220.0 | 220.0 | 220.0 |
| total | 1019.0 | 1019.0 | 1019.0 | 1019.0 | 1020.0 | 1020.0 | 1020.0 | 1020.0 |

| Example | 30 | 31 | 32 | 33 | 34 | 35 | 36 | 37 |
|---|---|---|---|---|---|---|---|---|
| pyraclostrobin | 100.0 | 100.0 | 100.0 | 100.0 | 100.0 | 100.0 | 100.0 | 100.0 |
| Solvesso 200 ND | 125.2 | 100.1 | 125.2 | 100.1 | 125.2 | 125.2 | 100.1 | 125.2 |
| Solvesso 150 ND | | | | | | | | |
| benzyl alcohol | | | | | | | | |
| acetophenone | 87.6 | 100.1 | 87.6 | 100.1 | 87.6 | 87.6 | 100.1 | 87.6 |
| γ-butyrolactone | 87.6 | 100.1 | 87.6 | 100.1 | 87.6 | 87.6 | 100.1 | 87.6 |
| Purasolv NPL | | | | | | | | |
| emulsifier 15 | | | | | | | | |
| emulsifier 16 | 87.4 | | 87.4 | | | 87.4 | 25.0 | |
| emulsifier 18 | | | 87.4 | | 87.4 | 87.4 | 124.8 | 87.4 |
| emulsifier 11 | | | 75.0 | | 75.0 | | | |
| emulsifier 12 | 75.0 | | | 100.0 | | | | |
| emulsifier 7 | | | | | | | | 75.0 |
| emulsifier 13 | | | | | | | | |
| emulsifier 2 | | 100.0 | | | | 75.0 | 100.0 | |
| emulsifier 14 | 87.4 | | | | 87.4 | | | 87.4 |
| emulsifier 8 | | 25.0 | | 25.0 | | | | |
| propylene glycol | 150.0 | 150.0 | 150.0 | 150.0 | 150.0 | 150.0 | 150.0 | 150.0 |
| deionized water | 250.0 | 250.0 | 250.0 | 250.0 | 250.0 | 250.0 | 250.0 | 250.0 |
| total | 1050.0 | 1050.0 | 1050.0 | 1050.0 | 1050.0 | 1050.0 | 1050.0 | 1050.0 |

| Example | 38 | 39 | 40 | 41 | 42 | 43 | 44 |
|---|---|---|---|---|---|---|---|
| pyraclostrobin | 100.0 | 100.0 | 100.0 | 100.0 | 100.0 | 100.0 | 100.0 |
| Solvesso 200 ND | 121.7 | 100.1 | 100.1 | 100.1 | 100.1 | 125.2 | 100.0 |
| Solvesso 150 ND | | | | | | | |
| benzyl alcohol | | | | | | | |
| acetophenone | 89.0 | 100.1 | 100.1 | 100.1 | 100.1 | 87.6 | 100.0 |
| γ-butyrolactone | 89.0 | 100.1 | 100.1 | 100.1 | 100.1 | 87.6 | 100.0 |
| Purasolv NPL | | | | | | | |
| emulsifier 15 | | | | | | | |
| emulsifier 16 | 90.7 | 25.0 | 25.0 | 25.0 | 25.0 | 87.4 | 25.0 |
| emulsifier 18 | 90.7 | 124.8 | 124.8 | 124.8 | | 87.4 | 175.0 |
| emulsifier 11 | 68.8 | | | 100.0 | | | |
| emulsifier 12 | | | 100.0 | | | | |

TABLE 2-continued

| Formulations (the numeric values are amounts in gram) | | | | | | | |
|---|---|---|---|---|---|---|---|
| emulsifier 7 | | 100.0 | | | 50.0 | 75.0 | |
| emulsifier 13 | | | | | | | 50.0 |
| emulsifier 2 | | | | | | | |
| emulsifier 14 | | | | | | | |
| emulsifier 8 | | | | | 174.8 | | |
| propylene glycol | 150.0 | 150.0 | 150.0 | 150.0 | 150.0 | 150.0 | 150.0 |
| deionized water | 250.0 | 250.0 | 250.0 | 250.0 | 250.0 | 250.0 | 250.0 |
| total | 1050.0 | 1050.0 | 1050.0 | 1050.0 | 1050.0 | 1050.0 | 1050.0 |

TABLE 3

Dilution and storage stabilities

| Example | Concentrate | −10° C. | 54° C. | Dilution 1:100, 2 h |
|---|---|---|---|---|
| 1 | ch | ch | ch | ch |
| 2 | ch | ch | ch | e |
| 3 | ch | ch | ch | oh |
| 4 | ch | ch | ch | e |
| 6 | ch | ch | ch | th |
| 7 | ch | ch | ch | th |
| 10 | ch | ch | ch | ch |
| 11 | ch | ch | ch | th |
| 12 | ch | ch | ch | e |
| 13 | ch | ch | ch | ch |
| 16 | ch | ch | ch | th |
| 18 | ch | solid | ch | th |
| 5 | ch | ch | ch | e |
| 8 | ch | ch | ch | th |
| 9 | ch | ch | ch | e |
| 22 | ch | ch | ch | e |
| 23 | ch | ch | ch | e |
| 24 | ch | ch | ch | e |
| 25 | ch | ch | ch | e |
| 36 | ch | ch | ch | e |
| 39 | ch | ch | ch | e |
| 40 | ch | ch | ch | e |
| 41 | ch | ch | ch | e |
| 43 | ch | ch | ch | e |

TABLE 4

Tests with respect to fungicidal action

| | Fungicidal action (relative infection exemplary vs. standard formulation EW/EC) | | |
|---|---|---|---|
| Example # | 200 ppm | 400 ppm | 600 ppm |
| 1 | 0.34 | 0.03 | 0.02 |
| 2 | 0.28 | 0.12 | 0.10 |
| 3 | 0.36 | 0.18 | 0.14 |
| 4 | 0.38 | 0.18 | 0.10 |
| 5 | 0.71 | 0.11 | 0.13 |
| 8 | 0.81 | 0.16 | 0.13 |
| 9 | 0.81 | 0.19 | 0.07 |
| 24 | 0.81 | 0.26 | 0.07 |
| | 63 ppm | 250 ppm | 1000 ppm |
| 36 | 0.56 | 0.14 | 0.05 |
| 39 | 0.69 | 0.17 | 0.05 |
| 40 | 0.81 | 0.33 | 0.08 |
| 41 | 0.71 | 0.19 | 0.05 |
| 43 | 0.58 | 0.09 | 0.00 |

The invention claimed is:

1. A liquid formulation for crop protection comprising
a) from 1 to 40% by weight of pyraclostrobin;
b) from 3 to 30% by weight of at least one organic solvent LM1 having a solubility in water of less than 2 g/l at 20° C.;
c) from 1 to 60% by weight of at least one organic solvent LM2 having a solubility in water of at least 2 g/l at 20° C., where LM2 comprises at least one solvent LM2.1 having a solubility in water of more than 200 g/l at 20° C. and optionally at least one solvent LM2.2 having a solubility in water from 2 to 200 g/l at 20° C., wherein the weight ratio of solvent LM2 to pyraclostrobin is from 0.1:1 to 10:1;
d) from 1 to 25% by weight of at least one anionic surfactant OS1;
e) from 1 to 25% by weight of at least one nonionic surfactant OS2; and
f) from 10 to 40% by weight of water.

2. The formulation according to claim 1 where LM2 comprises at least one solvent LM2.2.

3. The formulation of claim 1 where LM2.2 is selected from among solvents having a solubility in water of from 2 to 100 g/l at 20° C.

4. The formulation of claim 1 where LM2 comprises at least two solvents LM2.1 having a solubility in water of more than 200 g/l at 20° C.

5. The formulation of claim 1 where the solvents LM2.1 are selected from the group consisting of dimethyl sulfoxide, $C_2$-$C_4$-alkylene carbonates, N,N'-dimethyl-$C_3$-$C_4$-alkyleneureas, $C_3$-$C_5$-lactones, N-methyl-$C_3$-$C_5$-lactams, tri-$C_1$-$C_4$-alkyl phosphates, $C_1$-$C_3$-alkanols, mono-, di- and tri-($C_1$-$C_4$-alkyloxy)-$C_1$-$C_4$-alkanols, aliphatic $C_2$-$C_8$-diols, aliphatic $C_3$-$C_{12}$-triols, $C_4$-$C_8$-alkanecarboxylic esters carrying at least one hydroxyl group and tetrahydrofurfuryl alcohol.

6. The formulation of claim 1 where at least one solvent LM2.1 is selected from the group consisting of $C_3$-$C_5$-lactones, hydroxylated ($C_4$-$C_8$)-alkanecarboxylic esters, $C_1$-$C_3$-alkanols, $C_2$-$C_8$-alkanediols and $C_3$-$C_{12}$-alkanetriols.

7. The formulation of claim 1 where the solvents LM2.2 are selected from the group consisting of alkoxyalkyl $C_5$-$C_{12}$-alkanecarboxylates, alkyl $C_5$-$C_9$-alkanecarboxylates, $C_5$-$C_9$-dialkyl dicarboxylates, $C_5$-$C_9$-ketones, $C_5$-$C_9$-alkanediol alkanoates, $C_5$-$C_9$-alkanetriol alkanoates, $C_4$-$C_7$ alkanols, aliphatic $C_7$-$C_{10}$-diols, aliphatic $C_{11}$-$C_{15}$-triols, $C_5$-$C_9$-cycloalkyl alcohols, $C_5$-$C_9$-arylalkyl alcohols and $C_5$-$C_9$-aryloxyalkyl alcohols.

8. The formulation of claim 1 where the at least one solvent LM2.2 is selected from the group consisting of $C_5$-$C_9$-ketones and $C_5$-$C_9$-arylalkyl alcohols.

9. The formulation of claim 1 where the at least one solvent LM1 is selected from the group consisting of aliphatic, aromatic or cycloaliphatic hydrocarbons having boiling points of from 100 to 310° C., $C_8$-$C_{20}$-alkylphenols, $C_8$-$C_{20}$-alkanols, alkyl $C_{10}$-$C_{20}$-alkanecarboxylates, alkyl $C_{12}$-$C_{28}$-cycloalkanecarboxylates, dialkyl $C_{12}C_{28}$-cycloalkanedicarboxylates, $C_{10}$-$C_{15}$-dialkyl dicarboxylates, $C_{25}$-$C_{35}$-alkanetriol alkanoates, N-$C_8$-$C_{20}$-alkylpyrrolidone, and $C_8$-$C_{26}$-fatty acids, or their dialkyl amides or their alkyl esters.

10. The formulation according to claim 9 where the at least one solvent LM1 is selected from the group consisting of aliphatic, aromatic and cycloaliphatic hydrocarbons having boiling points of from 100 to 310° C.

11. The formulation of claim 1 where the at least one nonionic surfactant OS2 is selected from the group consisting of monofatty acid esters of polyhydroxylated compounds and compounds having at least one oligo-$C_2$-$C_4$-alkylene oxide group.

12. The formulation according to claim 11 where the at least one nonionic surfactant OS2 is selected from the group consisting of homo- or co-oligomers of $C_2$-$C_4$-alkylene oxides, oligo-$C_2$-$C_4$-alkylene oxide $C_1$-$C_{16}$-alkylbenzene ethers, oligo-$C_2$-$C_4$-alkylene oxide mono-, di- or tristyrylphenyl ethers, sorbitan monofatty acid esters, $C_2$-$C_4$-alkoxylated sorbitan monofatty acid esters and compounds of the formula I:

R—[OA]$_n$-OR'  (I),

in which
n denotes the average number of repeat units [OA] in the range of from 2 to 50,
each A in each case independently is ethanediyl, propane-1,2-diyl, butane-1,2-diyl or 2-methylpropane-1,2-diyl,
R is straight-chain or branched $C_8$-$C_{24}$-alkyl or $C_8$-$C_{24}$-alkenyl, and
R' is H, $C_1$-$C_8$-alkyl, CHO or $C_1$-$C_8$-alkylcarbonyl.

13. The formulation of claim 1 where OS2 comprises at least one nonionic surfactant having an HLB value of at most 13 and at least one nonionic surfactant having an HLB value of more than 13.

14. The formulation of claim 12 where OS2 comprises at least one nonionic surfactant having an HLB value of at most 13 selected from the group consisting of sorbitan monofatty acid esters and compounds of the formula I:

R—[OA]$_n$-OR'  (I),

in which
n denotes the average number of repeat units [OA] in the range of from 2 to 20,
each A in each case independently is ethanediyl, propane-1,2-diyl, butane-1,2-diyl or 2-methylpropane-1,2-diyl,
R is $C_8$-$C_{24}$-alkyl or $C_8$-$C_{24}$-alkenyl, and
R' is H, $C_1$-$C_8$-alkyl, CHO or $C_1$-$C_8$-alkylcarbonyl.

15. The formulation of claim 12 where OS2 comprises at least one nonionic surfactant having an HLB value of more than 13 selected from the group consisting of homo- or co-oligomers of $C_2$-$C_4$-alkylene oxides, oligo-$C_2$-$C_4$-alkylene oxide $C_1$-$C_{16}$-alkylbenzene ethers, oligo-$C_2$-$C_4$-alkylene oxide mono-, di- or tri-styrylphenyl ethers, $C_2$-$C_4$-alkoxylated sorbitan monofatty acid esters and compounds of the formula I:

R—[OA]$_n$-OR'  (I),

in which
n denotes the average number of repeat units [OA] in the range of from 8 to 50,
each A in each case independently is ethanediyl or propane-1,2-diyl,
R is $C_8$-$C_{24}$-alkyl or $C_8$-$C_{24}$-alkenyl, and
R' is H, $C_1$-$C_8$-alkyl, CHO or $C_1$-$C_8$-alkylcarbonyl.

16. The formulation of claim 1 where the at least one solvent LM2 has a solubility in water of at least 4 g/l at 20° C.

17. The formulation of claim 1 where the at least one solvent LM1 has a solubility in water of less than 1 g/l at 20° C.

18. The formulation of claim 1, additionally comprising at least one organic colorant.

19. The formulation of claim 1, additionally comprising at least one further pesticide selected from the group consisting of fungicides, insecticides and herbicides.

20. A method for treatment of plants or seed, wherein plants or seed are/is treated with an effective amount of a formulation of claim 1.

21. A method for controlling phytopathogenic organisms, comprising the bringing into contact of the phytopathogenic organisms, or of plants, of soil or of the environment in which the phytopathogenic organisms grow with an effective amount of a formulation of claim 1.

22. The method of claim 20 where the formulation is diluted with water prior to the treatment of the plants or the seed.

23. The method of claim 20, where the treatment or bringing into contact is by spraying.

* * * * *